United States Patent
Silver et al.

(10) Patent No.: US 11,545,235 B2
(45) Date of Patent: Jan. 3, 2023

(54) SYSTEM AND METHOD FOR THE COMPUTATIONAL PREDICTION OF EXPRESSION OF SINGLE-GENE PHENOTYPES

(71) Applicant: Ancestry.com DNA, LLC, Lehi, UT (US)

(72) Inventors: Lee M. Silver, New York, NY (US); Adam Cohn, Reston, VA (US); Ari Julian Silver, New York, NY (US)

(73) Assignee: Ancestry.com DNA, LLC, Lehi, UT (US)

( * ) Notice: Subject to any disclaimer, the term of this patent is extended or adjusted under 35 U.S.C. 154(b) by 1269 days.

(21) Appl. No.: 14/649,796

(22) PCT Filed: Dec. 5, 2013

(86) PCT No.: PCT/US2013/073415
§ 371 (c)(1),
(2) Date: Jun. 4, 2015

(87) PCT Pub. No.: WO2014/089356
PCT Pub. Date: Jun. 12, 2014

(65) Prior Publication Data
US 2015/0317432 A1 Nov. 5, 2015

Related U.S. Application Data

(60) Provisional application No. 61/733,600, filed on Dec. 5, 2012.

(51) Int. Cl.
*G01N 33/48* (2006.01)
*G16B 20/20* (2019.01)
*G16B 20/00* (2019.01)

(52) U.S. Cl.
CPC .......... *G16B 20/20* (2019.02); *G16B 20/00* (2019.02)

(58) Field of Classification Search
CPC .................................................. G06F 19/18
See application file for complete search history.

(56) References Cited

U.S. PATENT DOCUMENTS

| | | |
|---|---|---|
| 2002/0123058 A1 | 9/2002 | Threadgill et al. |
| 2003/0059808 A1 | 3/2003 | Liu et al. |
| 2004/0030503 A1 | 2/2004 | Arouh et al. |
| 2004/0197797 A1 | 10/2004 | Inoko et al. |
| 2006/0111849 A1 | 5/2006 | Schadt et al. |
| 2007/0185656 A1 | 8/2007 | Schadt |
| 2009/0017452 A1* | 1/2009 | Ratain ............... C12Q 1/6886 435/6.11 |
| 2009/0099789 A1* | 4/2009 | Stephan .............. G06F 19/18 702/20 |
| 2010/0145981 A1 | 6/2010 | Wojcicki et al. |
| 2011/0010148 A1 | 1/2011 | Ragot et al. |
| 2011/0124515 A1 | 5/2011 | Silver |
| 2011/0312534 A1 | 12/2011 | Kayser et al. |
| 2012/0034613 A1* | 2/2012 | Gopaul ............... A61K 45/06 435/6.12 |
| 2012/0215458 A1 | 8/2012 | Marcotte et al. |
| 2015/0363546 A1 | 12/2015 | Delaney et al. |
| 2016/0314245 A1 | 10/2016 | Silver et al. |

FOREIGN PATENT DOCUMENTS

| | | | |
|---|---|---|---|
| WO | WO 1992/01066 | 1/1992 | |
| WO | WO 2001/49104 | 7/2001 | |
| WO | WO 2002/35442 | 5/2002 | |
| WO | WO 2004/031912 | 4/2004 | |
| WO | WO-2004031912 A2 * | 4/2004 | ............ G06F 19/18 |
| WO | WO 2012/034030 | 3/2012 | |

OTHER PUBLICATIONS

Allen, Michael P., and Dominic J. Tildesley. Computer simulation of liquids. Oxford university press, 1987.*
Stephens et al. "A New Statistical Method for Haplotype Reconstruction from Population Data," (Am. J. Hum. Gemet, vol. 68 (2001) pp. 978-989).*
Baskovich et al. "Expanded genetic screening panel for the Ashkenazi Jewish population", Genetics in Medicine, 2016, vol. 18, No. 5, pp. 522-528.
Li, et al., "Generating Samples for Association Studies Based on HapMap Data", BioMed Central, BMC Bioinformatics, Jan. 24, 2008, vol. 9, No. 44, pp. 1-13.
Silver et al. "Carrier Screening is a Deficient Strategy for Determining Sperm Donor Eligibility and Reducing Risk of Disease in Recipient Children", Genetic Testing and Molecular Biomarkers, 2016, vol. 20, No. 6, pp. 276-284.
Srinivasan et al. "A universal carrier test for the long tail of Mendelian disease", Reproductive BioMedicine Online, 2010, pp. 537-551.
Burke et al. "Genetic Screening", Epidemiologic Reviews, Jun. 27, 2011, vol. 33, pp. 148-164.
Callum et al. "Spinal muscular atrophy (SMA) after conception using gametes from anonymous donors: recommendations for the future", Fertility and Sterility, Feb. 2010, vol. 93, No. 93, pp. 1006.e1-1006.e2.
Eypasch et al. "Probability of adverse events that have not yet occurred: a statistical reminder", Fertility and Sterility, Sep. 2, 1995, vol. 311, No. 93, pp. 619-620.

(Continued)

*Primary Examiner* — Anna Skibinsky
(74) *Attorney, Agent, or Firm* — Fenwick & West LLP

(57) ABSTRACT

In accordance with an embodiment of the invention, a system and method is provided for determining a probability of a progeny having one or more phenotypes $Ph_j$ each associated with a single gene $Q_j$. A score sip may be assigned to each allele hip at a plurality of genetic loci (i) in a haploid genome profile $H^p$ of a parent (p). A plurality (Nj) of the alleles hkp (k=1, . . . , Nj) associated with the gene $Q_j$ may be identified. The scores sip may be mapped or indexed to gene-specific scores ŝj,kp associated with gene $Q_j$ for the plurality of (Nj) alleles hkp. A probability may be computed for altering the gene product from gene $Q_j$ in a progeny of the parent (p) to be a function of the gene-specific scores ŝj,kp.

24 Claims, 20 Drawing Sheets

(56) References Cited

OTHER PUBLICATIONS

Green et al. "Psychosocial aspects of genetic screening of pregnant women and newborns: a systematic review", Health Technology Assessment, 2004, vol. 8, No. 33, pp. 1-4.
Levenson, "Genetic discrimination lawsuit raises broader concerns about testing, privacy", American Journal of Medical Genetics, 2016, pp. 1111-1112.
Martin et al. "Comprehensive carrier genetic test using next-generation deoxyribonucleic acid sequencing in infertile couples wishing to conceive through assisted reproductive technology", Fertility and Sterility, Nov. 2015, vol. 104, No. 5, pp. 1286-1293.
Larson et al., "Validation of a high resolution NGS method for detecting spinal muscular atrophy carriers among phase 3 participants in the 1000 Genomes Project", BMC Medical Genetics, (2015), 16:100, pp. 1-14.
Picard Tools. Broad Institute, broadinstitute.github.io/picard/ ; printed on Mar. 14, 2017.
Samtools, GitHub Social Coding samtools.sourceforge.net/ , Last Modified: Sep. 12, 2012.
Wiki, Snakemake/Documentation snakemake.readthedocs.io/en/stable/ ; 2014-2016.
View Run & Lane Metrics, Illumina, BaseSpace Online Help support.illumina.com/help/BaseSpace_OLH_009008/Content/Vault/Informatics/Sequencing_Analysis/BS/swSEO_mBS_ViewRunSamplesList.htm; printed on Mar. 14, 2017.
The Variant Call Format (VCF) Version 4.2 Specification, Nov. 15, 2016 //github.com/samtools/hts-specs, pp. 1-28.
Genepeeks, Inc., GitHub, Inc. [US], github.com/GenePeeks; printed on Mar. 14, 2017.
Data Protection, Amazon Web Services, aws.amazon.coms3/faqs/#data-protection; printed on Mar. 14, 2017.
Burrows—Wheeler Aligner bio-bwa.sourcelorge.net/, Last Modified: Feb. 28, 2010.
Amazon EC2 Instance Types, Amazon Web Services aws.amazon.com/ec2/instance-types/; printed on Mar. 14, 2017.
Reads-to-variants workflows used at the Broad Institute, GATK Best Practices, Recommended workflows for variant discovery analysis with GATK, GATK sofware.broadinstitute.org/gatk/best-practices/; printed on Mar. 14, 2017.
GregoryFaust/samblaster, GitHub, Inc. [US] github.com/GregoryFaust/samblaster , Published on May 7, 2014.
HaplotypeCaller, Call germline SNPs and indels via local re-assembly of haplotypes, GATK sofware. broadinstitute.org/gatk/documentation/tooldocs/current/org_broadinstitute_qatk_tools_walkers_haptotypecaller_haplotypecaller.php; Feb. 9, 2017.
Resource at: support.illumina.com/content/dam/illumina-support/documents/downloads/software/bcl2fastq/bcl2fasto2-v2-18-software-guide-15051736-01.pdf; Apr. 2016.
BaseRecalibrator, Detect systematic errors in base quality scores, GATK Best Practices, GATK, software.broadinstitute.org/gatk/documentation/tooldocs/current/org_broadinstitute_gatk_tools_walkers_bgsr_BaseRecalibrator.php; Jul. 29, 2017.
MongoDB Documentation docs.mongodb.com/?_ga=1.52591085.459598860.1467921146; Jul. 26, 2017.
HaplotypeCaller software.broadinstitute.org/gatk/documentation/tooldocs/current/org_broadinstitute_gatk_tools_walkers_haplotypecaller_HaplotypeCaller.php; Jul. 29, 2017.
Genome Profile DataBase gpdb.life.nthu.edu.tw/GPDB/index.php ; 2006.
Extended European Search Report for Application No. EP 13 85 9848 dated May 2, 2016.

* cited by examiner

| DISEASE | GENE | OMIM# |
|---|---|---|
| SEVERE COMBINED IMMUNODEFICIENCY, AR, T CELL-NEGATIVE, | ADA | 102700 |
| MYOADENYLATE DEAMINASE DEFICIENCY, MYOPATHY DUE TO | AMPD1 | 102770 |
| ANGELMAN SYNDROME AS | MECP2 | 105830 |
| PROTEASE INHIBITOR 1; PI | SERPINA1 | 107400 |
| MITOCHONDRIAL COMPLEX III DEFICIENCY | BCS1L | 124000 |
| MITOCHONDRIAL COMPLEX III DEFICIENCY | UQCRB | 124000 |
| MITOCHONDRIAL COMPLEX III DEFICIENCY | UQCRQ | 124000 |
| COCKAYNE SYNDROME, B; CSB | ERCC6 | 133540 |
| HEMOGLOBIN--ALPHA LOCUS 1; HBA1 | HBA1 | 141800 |
| HEMOGLOBIN--BETA LOCUS; HBB | HBB | 141900 |
| HYPERTROPHIC NEUROPATHY OF DEJERINE-SOTTAS. CMT3, CMT4F | EGR2 | 145900 |
| HYPERTROPHIC NEUROPATHY OF DEJERINE-SOTTAS. CMT3, CMT4F | MPZ | 145900 |
| HYPERTROPHIC NEUROPATHY OF DEJERINE-SOTTAS. CMT3, CMT4F | PMP22 | 145900 |
| HYPERTROPHIC NEUROPATHY OF DEJERINE-SOTTAS. CMT3, CMT4F | PRX | 145900 |
| THROMBOPHILIA DUE TO ACTIVATED PROTEIN C RESISTANCE | F5 | 188055 |
| DOWN SYNDROME | GATA1 | 190685 |
| ABETALIPOPROTEINEMIA; ABL | MTTP | 200100 |
| ACROCALLOSAL SYNDROME; ACLS | GLI3 | 200990 |
| CARPENTER SYNDROME | RAB23 | 201000 |
| ACYL-CoA DEHYDROGENASE, MEDIUM-CHAIN, DEFICIENCY OF | ACADM | 201450 |
| ACYL-CoA DEHYDROGENASE, LONG-CHAIN, DEFICIENCY OF | ACADL | 201460 |
| ACYL-CoA DEHYDROGENASE, SHORT-CHAIN, DEFICIENCY OF | ACADS | 201470 |
| ACYL-CoA DEHYDROGENASE, VERY LONG-CHAIN, DEFICIENCY OF | ACADVL | 201475 |
| LIPOID CONGENITAL ADRENAL HYPERPLASIA | CYP11A1 | 201710 |
| LIPOID CONGENITAL ADRENAL HYPERPLASIA | STAR | 201710 |
| CONGENITAL ADRENAL HYPERPLASIA, 21-HYDROXYLASE DEFICIENCY | CYP21A2 | 201910 |
| AFIBRINOGENEMIA, CONGENITAL | FGA | 202400 |
| AFIBRINOGENEMIA, CONGENITAL | FGB | 202400 |
| AFIBRINOGENEMIA, CONGENITAL | FGG | 202400 |
| ALKAPTONURIA | HGD | 203500 |
| ALPERS DIFFUSE CEREBRAL DEGENERATION WITH HEPATIC CIRRHOSIS | POLG | 203700 |
| ALPORT SYNDROME, AR | COL4A3 | 203780 |
| ALPORT SYNDROME, AR | COL4A4 | 203780 |
| ALSTROM SYNDROME; ALMS | ALMS1 | 203800 |
| CEROID LIPOFUSCINOSIS, NEURONAL, 3; CLN3 | CLN3 | 204200 |

Fig. 8

| DISEASE | GENE | OMIM# |
|---|---|---|
| CEROID LIPOFUSCINOSIS, NEURONAL, 2; CLN2 | TPP1 | 204500 |
| AMYOTROPHIC LATERAL SCLEROSIS 2, JUVENILE; ALS2 | ALS2 | 205100 |
| ANIRIDIA, CEREBELLAR ATAXIA, AND MENTAL DEFICIENCY | PAX6 | 206700 |
| ANTLEY-BIXLER SYNDROME; ABS | FGFR2 | 207410 |
| ARGININOSUCCINIC ACIDURIA | ASL | 207900 |
| ARTERIAL CALCIFICATION, GENERALIZED, OF INFANCY; GACI | ENPP1 | 208000 |
| ARTHROGRYPOSIS, RENAL DYSFUNCTION, AND CHOLESTASIS | VPS33B | 208085 |
| FETAL AKINESIA DEATION SEQUENCE; FADS | RAPSN | 208150 |
| ASPARTYLGLUCOSAMINURIA | AGA | 208400 |
| RENAL-HEPATIC-PANCREATIC DYSPLASIA; RHPD | NPHP3 | 208540 |
| ATAXIA-TELANGIECTASIA; AT | ATM | 208900 |
| EARLY-ONSET ATAXIA WITH OCULOMOTOR APRAXIA AND HYPOALBUMINEMIA | APTX | 208920 |
| 3-METHYLCROTONYL-CoA CARBOXYLASE 2 DEFICIENCY | MCCC2 | 210210 |
| SECKEL SYNDROME 1 | ATR | 210600 |
| BLOOM SYNDROME; BLM | BLM | 210900 |
| CHOLESTASIS, PROGRESSIVE FAMILIAL INTRAHEPATIC 1; PFIC1 | ATP8B1 | 211600 |
| C SYNDROME | CD96 | 211750 |
| CONGENITAL DISORDER OF GLYCOSYLATION, Ia; CDG1A | PMM2 | 212065 |
| CONGENITAL DISORDER OF GLYCOSYLATION, IIa; CDG2A | MGAT2 | 212066 |
| MARTSOLF SYNDROME | RAB3GAP2 | 212720 |
| CEREBROTENDINOUS XANTHOMATOSIS | CYP27A1 | 213700 |
| CEREBROOCULOFACIOSKELETAL SYNDROME 1; COFS1 | ERCC6 | 214150 |
| GRISCELLI SYNDROME, 1; GS1 | MYO5A | 214450 |
| CHEDIAK-HIGASHI SYNDROME; CHS | LYST | 214500 |
| BILE ACID SYNTHESIS DEFECT, CONGENITAL, 4 | AMACR | 214950 |
| CHONDRODYSPLASIA, BLOMSTRAND ; BOCD | PTH1R | 215045 |
| RHIZOMELIC CHONDRODYSPLASIA PUNCTATA, 1; RCDP1 | PEX7 | 215100 |
| HYDROPS-ECTOPIC CALCIFICATION-MOTH-EATEN SKELETAL DYSPLASIA | LBR | 215140 |
| OTOSPONDYLOMEGAEPIPHYSEAL DYSPLASIA; OSMED | COL11A2 | 215150 |
| OTOSPONDYLOMEGAEPIPHYSEAL DYSPLASIA; OSMED | COL2A1 | 215150 |
| CIRRHOSIS, FAMILIAL | KRT18 | 215600 |
| CIRRHOSIS, FAMILIAL | KRT8 | 215600 |
| CITRULLINEMIA, CLASSIC | ASS1 | 215700 |
| COCKAYNE SYNDROME, A; CSA | ERCC8 | 216400 |
| COHEN SYNDROME; COH1 | VPS13B | 216550 |
| PLASMINOGEN DEFICIENCY, I | PLG | 217090 |
| CORNEAL DYSTROPHY AND PERCEPTIVE DEAFNESS | SLC4A11 | 217400 |
| AGENESIS OF THE CORPUS CALLOSUM WITH PERIPHERAL NEUROPATHY; ACCPN | SLC12A6 | 218000 |
| FRASER SYNDROME | FRAS1 | 219000 |
| FRASER SYNDROME | FREM2 | 219000 |
| CUTIS LAXA, AR, I | EFEMP2 | 219100 |
| CUTIS LAXA, AR, I | FBLN5 | 219100 |

Fig. 8 cont.

| DISEASE | GENE | OMIM# |
|---|---|---|
| CUTIS LAXA, AR, II | ATP6V0A2 | 219200 |
| CYSTIC FIBROSIS; CF | CFTR | 219700 |
| CYSTINOSIS, ADULT NONNEPHROPATHIC | CTNS | 219750 |
| CYSTINOSIS, NEPHROPATHIC; CTNS | CTNS | 219800 |
| CYSTINOSIS, LATE-ONSET JUVENILE OR ADOLESCENT NEPHROPATHIC | CTNS | 219900 |
| LEIGH SYNDROME, FRENCH-CANADIAN ; LSFC | LRPPRC | 220111 |
| DEAFNESS, AR 1A | GJB2 | 220290 |
| JERVELL AND LANGE-NIELSEN SYNDROME 1; JLNS1 | KCNQ1 | 220400 |
| DONNAI-BARROW SYNDROME | LRP2 | 222448 |
| DIASTROPHIC DYSPLASIA | SLC26A2 | 222600 |
| NEUROPATHY, HEREDITARY SENSORY AND AUTONOMIC, III; HSAN3 | IKBKAP | 223900 |
| CEREBELLAR HYPOPLASIA AND MENTAL RETARDATION | VLDLR | 224050 |
| DYSSEGMENTAL DYSPLASIA, SILVERMAN-HANDMAKER ; DDSH | HSPG2 | 224410 |
| EHLERS-DANLOS SYNDROME, AR, CARDIAC VALVULAR | COL1A2 | 225320 |
| EHLERS-DANLOS SYNDROME, VII, AR | ADAMTS2 | 225410 |
| AICARDI-GOUTIERES SYNDROME 1; AGS1 | TREX1 | 225750 |
| PONTOCEREBELLAR HYPOPLASIA 4; PCH4 | TSEN54 | 225753 |
| EPIDERMOLYSIS BULLOSA DYSTROPHICA, AR; RDEB | COL7A1 | 226600 |
| EPIDERMOLYSIS BULLOSA, JUNCTIONAL, NON-HERLITZ | COL17A1 | 226650 |
| EPIDERMOLYSIS BULLOSA, JUNCTIONAL, NON-HERLITZ | ITGB4 | 226650 |
| EPIDERMOLYSIS BULLOSA, JUNCTIONAL, NON-HERLITZ | LAMA3 | 226650 |
| EPIDERMOLYSIS BULLOSA, JUNCTIONAL, NON-HERLITZ | LAMB3 | 226650 |
| EPIDERMOLYSIS BULLOSA, JUNCTIONAL, NON-HERLITZ | LAMC2 | 226650 |
| EPIDERMOLYSIS BULLOSA SIMPLEX WITH MUSCULAR DYSTROPHY | PLEC1 | 226670 |
| EPIDERMOLYSIS BULLOSA, JUNCTIONAL, HERLITZ | LAMA3 | 226700 |
| EPIDERMOLYSIS BULLOSA, JUNCTIONAL, HERLITZ | LAMB3 | 226700 |
| EPIDERMOLYSIS BULLOSA, JUNCTIONAL, HERLITZ | LAMC2 | 226700 |
| EPIDERMOLYSIS BULLOSA JUNCTIONALIS WITH PYLORIC ATRESIA | ITGA6 | 226730 |
| EPIDERMOLYSIS BULLOSA JUNCTIONALIS WITH PYLORIC ATRESIA | ITGB4 | 226730 |
| EPIPHYSEAL DYSPLASIA, MULTIPLE, WITH EARLY-ONSET DIABETES MELLITUS | EIF2AK3 | 226980 |
| FIBROMATOSIS, JUVENILE HYALINE | ANTXR2 | 228600 |
| FIBULAR APLASIA OR HYPOPLASIA | WNT7A | 228930 |
| BRITTLE CORNEA SYNDROME; BCS | ZNF469 | 229200 |
| FRUCTOSE INTOLERANCE, HEREDITARY | ALDOB | 229600 |
| FUCOSIDOSIS | FUCA1 | 230000 |
| GALACTOSEMIA | GALT | 230400 |
| GM1-GANGLIOSIDOSIS, I | GLB1 | 230500 |
| GM1-GANGLIOSIDOSIS, II | GLB1 | 230600 |
| GAUCHER DISEASE, I | GBA | 230800 |
| GAUCHER DISEASE, II | GBA | 230900 |
| GAUCHER DISEASE, III | GBA | 231000 |
| GELEOPHYSIC DYSPLASIA | ADAMTSL2 | 231050 |

Fig. 8 cont.

| DISEASE | GENE | OMIM# |
|---|---|---|
| 3-HYDROXYACYL-CoA DEHYDROGENASE DEFICIENCY | HADH | 231530 |
| ACHALASIA-ADDISONIANISM-ALACRIMA SYNDROME; AAA | AAAS | 231550 |
| GLUTARIC ACIDEMIA I | GCDH | 231670 |
| MULTIPLE ACYL-CoA DEHYDROGENASE DEFICIENCY; MADD | ETFA | 231680 |
| MULTIPLE ACYL-CoA DEHYDROGENASE DEFICIENCY; MADD | ETFB | 231680 |
| MULTIPLE ACYL-CoA DEHYDROGENASE DEFICIENCY; MADD | ETFDH | 231680 |
| GLYCOGEN STORAGE DISEASE I | G6PC3 | 232200 |
| GLYCOGEN STORAGE DISEASE Ib | SLC37A4 | 232220 |
| GLYCOGEN STORAGE DISEASE Ic | SLC37A4 | 232240 |
| GLYCOGEN STORAGE DISEASE II | GAA | 232300 |
| GLYCOGEN STORAGE DISEASE III | AGL | 232400 |
| GLYCOGEN STORAGE DISEASE IV | GBE1 | 232500 |
| HEMOCHROMATOSIS; HFE | HFE | 235200 |
| HEMOCHROMATOSIS; HFE | HFE2 | 235200 |
| HEPATIC VENOOCCLUSIVE DISEASE WITH IMMUNODEFICIENCY; VODI | SP110 | 235550 |
| HOMOCYSTINURIA | CBS | 236200 |
| HOMOCYSTINURIA DUE TO DEFICIENCY OF METHYLENETETRAHYDROFOLATE | MTHFR | 236250 |
| HYALINOSIS, INFANTILE SYSTEMIC | ANTXR2 | 236490 |
| WALKER-WARBURG SYNDROME; WWS | POMT1 | 236670 |
| WALKER-WARBURG SYNDROME; WWS | POMT2 | 236670 |
| HYDROLETHALUS SYNDROME 1 | HYLS1 | 236680 |
| CARBAMOYL PHOSPHATE SYNTHETASE I DEFICIENCY, HYPERAMMONEMIA | CPS1 | 237300 |
| N-ACETYLGLUTAMATE SYNTHASE DEFICIENCY | NAGS | 237310 |
| HYPERORNITHINEMIA-HYPERAMMONEMIA-HOMOCITRULLINURIA SYNDROME | SLC25A15 | 238970 |
| PAGET DISEASE, JUVENILE | TNFRSF11B | 239000 |
| AUTOIMMUNE POLYENDOCRINE SYNDROME, I; APS1 | AIRE | 240300 |
| BARTTER SYNDROME, ANTENATAL, 2 | KCNJ1 | 241200 |
| HYPOPARATHYROIDISM-RETARDATION-DYSMORPHISM SYNDROME; HRD | TBCE | 241410 |
| HYPOPHOSPHATASIA, CHILDHOOD | ALPL | 241510 |
| HYPOPHOSPHATEMIC RICKETS, AR | DMP1 | 241520 |
| HYPOPLASTIC LEFT HEART SYNDROME | GJA1 | 241550 |
| ICHTHYOSIS, LAMELLAR, 1; LI1 | TGM1 | 242300 |
| ICHTHYOSIS CONGENITA, HARLEQUIN FETUS | ABCA12 | 242500 |
| IMMUNODEFICIENCY-CENTROMERIC INSTABILITY-FACIAL ANOMALIES SYNDROME | DNMT3B | 242860 |
| ISOVALERIC ACIDEMIA; IVA | IVD | 243500 |
| JOHANSON-BLIZZARD SYNDROME; JBS | UBR1 | 243800 |
| KENNY-CAFFEY SYNDROME, 1; KCS | TBCE | 244460 |
| KRABBE DISEASE | GALC | 245200 |
| PYRUVATE DEHYDROGENASE E3-BINDING PROTEIN DEFICIENCY | PDHX | 245349 |

Fig. 8 cont.

| DISEASE | GENE | OMIM# |
|---|---|---|
| LACTIC ACIDOSIS, FATAL INFANTILE | SUCLG1 | 245400 |
| LARYNGOONYCHOCUTANEOUS SYNDROME; LOCS | LAMA3 | 245660 |
| DONOHUE SYNDROME | INSR | 246200 |
| 3-HYDROXY-3-METHYLGLUTARYL-CoA LYASE DEFICIENCY | HMGCL | 246450 |
| HYPOMAGNESEMIA, RENAL, WITH OCULAR INVOLVEMENT | CLDN19 | 248190 |
| MANNOSIDOSIS, ALPHA B, LYSOSOMAL | MAN2B1 | 248500 |
| MAPLE SYRUP URINE DISEASE Ia | BCKDHA | 248600 |
| MAPLE SYRUP URINE DISEASE, CLASSIC, IB | BCKDHB | 248600 |
| MAPLE SYRUP URINE DISEASE III | DLD | 248600 |
| Marinesco-Sjogren Syndrome | SIL1 | 248800 |
| MECKEL SYNDROME, 1; MKS1 | MKS1 | 249000 |
| FAMILIAL MEDITERRANEAN FEVER; FMF | MEFV | 249100 |
| METACHROMATIC LEUKODYSTROPHY DUE TO SAPOSIN B DEFICIENCY | PSAP | 249900 |
| METACHROMATIC LEUKODYSTROPHY | ARSA | 250100 |
| CARTILAGE-HAIR HYPOPLASIA; CHH | RMRP | 250250 |
| BETA-HYDROXYISOBUTYRYL CoA DEACYLASE, DEFICIENCY OF | HIBCH | 250620 |
| 3-METHYLGLUTACONIC ACIDURIA, I | AUH | 250950 |
| METHYLMALONIC ACIDURIA DUE TO METHYLMALONYL-CoA MUTASE DEFICIENCY | MUT | 251000 |
| METHYLMALONIC ACIDURIA, cblB | MMAB | 251110 |
| NIJMEGEN BREAKAGE SYNDROME | NBN | 251260 |
| MITOCHONDRIAL DNA DEPLETION SYNDROME, HEPATOCEREBRAL | C10ORF2 | 251880 |
| MITOCHONDRIAL DNA DEPLETION SYNDROME, HEPATOCEREBRAL | DGUOK | 251880 |
| MITOCHONDRIAL DNA DEPLETION SYNDROME, HEPATOCEREBRAL | MPV17 | 251880 |
| MOLYBDENUM COFACTOR DEFICIENCY | MOCS1 | 252150 |
| MOLYBDENUM COFACTOR DEFICIENCY | MOCS2 | 252150 |
| MUCOLIPIDOSIS II ALPHA/BETA | GNPTAB | 252500 |
| MUCOLIPIDOSIS III ALPHA/BETA | GNPTAB | 252600 |
| MUCOLIPIDOSIS IV | MCOLN1 | 252650 |
| MUCOPOLYSACCHARIDOSIS IIIA | SGSH | 252900 |
| MUCOPOLYSACCHARIDOSIS IIIC | HGSNAT | 252930 |
| MUCOPOLYSACCHARIDOSIS VI | ARSB | 253200 |
| MUCOPOLYSACCHARIDOSIS VII | GUSB | 253220 |
| MUCOPOLYSACCHARIDOSIS VIII | GNS | 253230 |
| MULIBREY NANISM | TRIM37 | 253250 |
| BIOTINIDASE DEFICIENCY | BTD | 253260 |
| MUSCLE-EYE-BRAIN DISEASE; MEB | FKRP | 253280 |
| MUSCLE-EYE-BRAIN DISEASE; MEB | POMGNT1 | 253280 |
| MULTIPLE PTERYGIUM SYNDROME, LETHAL | CHRNA1 | 253290 |
| MULTIPLE PTERYGIUM SYNDROME, LETHAL | CHRND | 253290 |
| MULTIPLE PTERYGIUM SYNDROME, LETHAL | CHRNG | 253290 |
| SPINAL MUSCULAR ATROPHY, I; SMA1 | SMN1 | 253300 |
| LETHAL CONGENITAL CONTRACTURE SYNDROME 1; LCCS1 | GLE1 | 253310 |
| SPINAL MUSCULAR ATROPHY, III; SMA3 | SMN1 | 253400 |

Fig. 8 cont.

| DISEASE | GENE | OMIM# |
| --- | --- | --- |
| SPINAL MUSCULAR ATROPHY, II; SMA2 | SMN1 | 253550 |
| FUKUYAMA CONGENITAL MUSCULAR DYSTROPHY; FCMD | FKTN | 253800 |
| MYOCLONIC EPILEPSY OF LAFORA | EPM2A | 254780 |
| MYOCLONIC EPILEPSY OF LAFORA | NHLRC1 | 254780 |
| MYOCLONIC EPILEPSY OF UNVERRICHT AND LUNDBORG | CSTB | 254800 |
| CARNITINE PALMITOYLTRANSFERASE II DEFICIENCY, LATE-ONSET | CPT2 | 255110 |
| CARNITINE PALMITOYLTRANSFERASE I DEFICIENCY | CPT1A | 255120 |
| MYXOMA, INTRACARDIAC | PRKAR1A | 255960 |
| NEMALINE MYOPATHY 2; NEM2 | NEB | 256030 |
| ATELOSTEOGENESIS, II; AOII | SLC26A2 | 256050 |
| NEPHRONOPHTHISIS 1; NPHP1 | NPHP1 | 256100 |
| NEPHROSIS 1, CONGENITAL, FINNISH ; NPHS1 | NPHS1 | 256300 |
| NEPHROTIC SYNDROME, EARLY-ONSET, WITH DIFFUSE MESANGIAL SCLEROSIS | WT1 | 256370 |
| NEURAMINIDASE DEFICIENCY | NEU1 | 256550 |
| NEUROAXONAL DYSTROPHY, INFANTILE; INAD1 | PLA2G6 | 256600 |
| ELEJALDE DISEASE | MYO5A | 256710 |
| CEROID LIPOFUSCINOSIS, NEURONAL, 1; CLN1 | PPT1 | 256730 |
| CEROID LIPOFUSCINOSIS, NEURONAL, 5; CLN5 | CLN5 | 256731 |
| INSENSITIVITY TO PAIN, CONGENITAL, WITH ANHIDROSIS; CIPA | NTRK1 | 256800 |
| NAVAJO NEUROHEPATOPATHY; NN | MPV17 | 256810 |
| NIEMANN-PICK DISEASE, A | SMPD1 | 257200 |
| NIEMANN-PICK DISEASE, C1; NPC1 | NPC1 | 257220 |
| LISSENCEPHALY 2; LIS2 | RELN | 257320 |
| ODONTOONYCHODERMAL DYSPLASIA; OODD | WNT10A | 257980 |
| 3-METHYLGLUTACONIC ACIDURIA, III | OPA3 | 258501 |
| OSTEOPETROSIS, AR 1; OPTB1 | TCIRG1 | 259700 |
| OSTEOPETROSIS, AR 5; OPTB5 | OSTM1 | 259720 |
| OSTEOPETROSIS, AR 3; OPTB3 | CA2 | 259730 |
| OSTEOPOROSIS-PSEUDOGLIOMA SYNDROME; OPPG | LRP5 | 259770 |
| RAINE SYNDROME; RNS | FAM20C | 259775 |
| HYPEROXALURIA, PRIMARY, I | AGXT | 259900 |
| HYPEROXALURIA, PRIMARY, II | GRHPR | 260000 |
| SHWACHMAN-DIAMOND SYNDROME; SDS | SBDS | 260400 |
| D-BIFUNCTIONAL PROTEIN DEFICIENCY | HSD17B4 | 261515 |
| PHENYLKETONURIA; PKU | PAH | 261600 |
| GLYCOGEN STORAGE DISEASE OF HEART, LETHAL CONGENITAL | PRKAG2 | 261740 |
| ACHROMATOPSIA 3; ACHM3 | CNGB3 | 262300 |
| PITUITARY DWARFISM III | HESX1 | 262600 |
| PITUITARY DWARFISM III | LHX3 | 262600 |
| PITUITARY DWARFISM III | POU1F1 | 262600 |
| PITUITARY DWARFISM III | PROP1 | 262600 |
| POLYCYSTIC KIDNEY DISEASE, AR; ARPKD | PKHD1 | 263200 |
| PORPHYRIA, CONGENITAL ERYTHROPOIETIC | UROS | 263700 |
| PSEUDOHYPOALDOSTERONISM, I, AR; PHA1 | SCNN1A | 264350 |
| PSEUDOHYPOALDOSTERONISM, I, AR; PHA1 | SCNN1B | 264350 |

Fig. 8 cont.

| DISEASE | GENE | OMIM# |
|---|---|---|
| PSEUDOHYPOALDOSTERONISM, I, AR; PHA1 | SCNN1G | 264350 |
| PEROXISOMAL ACYL-CoA OXIDASE DEFICIENCY | ACOX1 | 264470 |
| VITAMIN D-DEPENDENT RICKETS, I | CYP27B1 | 264700 |
| MULTIPLE PTERYGIUM SYNDROME, ESCOBAR | CHRNG | 265000 |
| PULMONARY ALVEOLAR MICROLITHIASIS | SLC34A2 | 265100 |
| SURFACTANT METABOLISM DYSFUNCTION, PULMONARY, 1; SMDP1 | SFTPB | 265120 |
| NEWBORN PULMONARY HYPERTENSION, FAMILIAL PERSISTENT | CPS1 | 265380 |
| PULMONARY VENOOCCLUSIVE DISEASE; PVOD | BMPR2 | 265450 |
| PYCNODYSOSTOSIS | CTSK | 265800 |
| GLUTATHIONE SYNTHETASE DEFICIENCY | GSS | 266130 |
| PYRUVATE CARBOXYLASE DEFICIENCY | PC | 266150 |
| PYRUVATE KINASE DEFICIENCY OF RED CELLS | PKLR | 266200 |
| CONGENITAL DISORDER OF GLYCOSYLATION, IIc; CDG2C | SLC35C1 | 266265 |
| SENIOR-LOKEN SYNDROME 1; SLSN1 | NPHP1 | 266900 |
| RENAL TUBULAR DYSGENESIS; RTD | ACE | 267430 |
| RENAL TUBULAR DYSGENESIS; RTD | AGT | 267430 |
| RENAL TUBULAR DYSGENESIS; RTD | AGTR1 | 267430 |
| RENAL TUBULAR DYSGENESIS; RTD | REN | 267430 |
| RESPIRATORY DISTRESS SYNDROME IN PREMATURE INFANTS | SFTPA1 | 267450 |
| RESPIRATORY DISTRESS SYNDROME IN PREMATURE INFANTS | SFTPB | 267450 |
| RESPIRATORY DISTRESS SYNDROME IN PREMATURE INFANTS | SFTPC | 267450 |
| ROBERTS SYNDROME; RBS | ESCO2 | 268300 |
| SANDHOFF DISEASE | HEXB | 268800 |
| SCHNECKENBECKEN DYSPLASIA | SLC35D1 | 269250 |
| INFANTILE SIALIC ACID STORAGE DISORDER | SLC17A5 | 269920 |
| SJOGREN-LARSSON SYNDROME; SLS | ALDH3A2 | 270200 |
| SMITH-LEMLI-OPITZ SYNDROME; SLOS | DHCR7 | 270400 |
| INSULIN-LIKE GROWTH FACTOR I, RESISTANCE TO | IGF1 | 270450 |
| SPASTIC ATAXIA, CHARLEVOIX-SAGUENAY ; SACS | SACS | 270550 |
| INFANTILE-ONSET SPINOCEREBELLAR ATAXIA; IOSCA | C10ORF2 | 271245 |
| CANAVAN DISEASE | ASPA | 271900 |
| STRIATONIGRAL DEGENERATION, INFANTILE; SNDI | NUP62 | 271930 |
| SUCCINIC SEMIALDEHYDE DEHYDROGENASE DEFICIENCY | ALDH5A1 | 271980 |
| SULFOCYSTEINURIA | SUOX | 272300 |
| TAY-SACHS DISEASE; TSD | HEXA | 272800 |
| TETRA-AMELIA, AR | WNT3 | 273395 |
| THROMBOTIC THROMBOCYTOPENIC PURPURA, CONGENITAL; TTP | ADAMTS13 | 274150 |
| DIHYDROPYRIMIDINE DEHYDROGENASE; DPYD | DPYD | 274270 |
| PENDRED SYNDROME; PDS | SLC26A4 | 274600 |
| HYPOTHYROIDISM, CONGENITAL, NONGOITROUS, 4; CHNG4 | TSHB | 275100 |
| TIGHT SKIN CONTRACTURE SYNDROME, LETHAL | LMNA | 275210 |
| TIGHT SKIN CONTRACTURE SYNDROME, LETHAL | ZMPSTE24 | 275210 |

Fig. 8 cont.

| DISEASE | GENE | OMIM# |
|---|---|---|
| TYROSINEMIA, I | FAH | 276700 |
| ULNA AND FIBULA, ABSENCE OF | WNT7A | 276820 |
| USHER SYNDROME, I | MYO7A | 276900 |
| USHER SYNDROME, IIA; USH2A | USH2A | 276901 |
| USHER SYNDROME, III; USH3 | CLRN1 | 276902 |
| USHER SYNDROME, IC; USH1C | USH1C | 276904 |
| SPONDYLOCOSTAL DYSOSTOSIS, AR 1; SCDO1 | DLL3 | 277300 |
| METHYLMALONIC ACIDURIA AND HOMOCYSTINURIA, cblC | MMACHC | 277400 |
| VITAMIN D-DEPENDENT RICKETS, II | VDR | 277440 |
| VITAMIN E, FAMILIAL ISOLATED DEFICIENCY OF; VED | TTPA | 277460 |
| PONTOCEREBELLAR HYPOPLASIA 2A; PCH2A | TSEN54 | 277470 |
| WAARDENBURG-SHAH SYNDROME | EDN3 | 277580 |
| WAARDENBURG-SHAH SYNDROME | EDNRB | 277580 |
| WAARDENBURG-SHAH SYNDROME | SOX10 | 277580 |
| WILSON DISEASE | ATP7B | 277900 |
| XERODERMA PIGMENTOSUM, COMPLEMENTATION GROUP A; XPA | XPA | 278700 |
| XERODERMA PIGMENTOSUM, COMPLEMENTATION GROUP D; XPD | ERCC2 | 278730 |
| XERODERMA PIGMENTOSUM, COMPLEMENTATION GROUP E | DDB2 | 278740 |
| XERODERMA PIGMENTOSUM, COMPLEMENTATION GROUP F; XPF | ERCC4 | 278760 |
| XERODERMA PIGMENTOSUM, COMPLEMENTATION GROUP G; XPG | ERCC5 | 278780 |
| DE SANCTIS-CACCHIONE SYNDROME | ERCC6 | 278800 |
| DE SANCTIS-CACCHIONE SYNDROME | XPA | 278800 |
| CORPUS CALLOSUM, AGENESIS OF, WITH ABNORMAL GENITALIA | ARX | 300004 |
| DOSAGE-SENSITIVE SEX REVERSAL; DSS | NR0B1 | 300018 |
| INTESTINAL PSEUDOOBSTRUCTION, NEURONAL, CHRONIC IDIOPATHIC, XLR | FLNA | 300048 |
| LISSENCEPHALY, XLR, 1; LISX1 | DCX | 300067 |
| CARDIOMYOPATHY, DILATED, 3A; CMD3A | TAZ | 300069 |
| ADRENOLEUKODYSTROPHY; ALD | ABCD1 | 300100 |
| SIMPSON-GOLABI-BEHMEL SYNDROME, 2 | OFD1 | 300209 |
| LISSENCEPHALY, XLR, 2 LISX2 | ARX | 300215 |
| MENTAL RETARDATION, XLR, SYNDROMIC 10; MRXS10 | HSD17B10 | 300220 |
| HOYERAAL-HREIDARSSON SYNDROME; HHS | DKC1 | 300240 |
| MENTAL RETARDATION, XLR, SYNDROMIC, CHRISTIANSON | SLC9A6 | 300243 |
| ECTODERMAL DYSPLASIA, HYPOHIDROTIC, WITH IMMUNE DEFICIENCY | IKBKG | 300291 |
| OSTEOPETROSIS, LYMPHEDEMA, ECTODERMAL DYSPLASIA, ANHIDROSIS, IMMUNODEFICIENCY | IKBKG | 300301 |
| LESCH-NYHAN SYNDROME; LNS | HPRT1 | 300322 |
| CREATINE DEFICIENCY SYNDROME, XLR | SLC6A8 | 300352 |
| SEVERE COMBINED IMMUNODEFICIENCY, XLR; SCIDX1 | IL2RG | 300400 |
| AGENESIS OF CORPUS CALLOSUM WITH MENTAL RETARDATION, OCULAR COLOBOMA | IGBP1 | 300472 |

Fig. 8 cont.

| DISEASE | GENE | OMIM# |
|---|---|---|
| ALLAN-HERNDON-DUDLEY SYNDROME AHDS | SLC16A2 | 300523 |
| EPILEPTIC ENCEPHALOPATHY, EARLY INFANTILE, 2 | CDKL5 | 300672 |
| ENCEPHALOPATHY, NEONATAL SEVERE, DUE TO MECP2 MUTATIONS | MECP2 | 300673 |
| AGAMMAGLOBULINEMIA, XLR XLA | BTK | 300755 |
| WISKOTT-ALDRICH SYNDROME; WAS | WAS | 301000 |
| α-THALASSEMIA/MENTAL RETARDATION SYNDROME,NONDELETION , XLR ATRX | ATRX | 301040 |
| FABRY DISEASE | GLA | 301500 |
| SPINAL MUSCULAR ATROPHY, XLR 2; SMAX2 | UBA1 | 301830 |
| ARTS SYNDROME; ARTS | PRPS1 | 301835 |
| CARDIOMYOPATHY, DILATED, 3B; CMD3B | DMD | 302045 |
| BARTH SYNDROME; BTHS | TAZ | 302060 |
| CHONDRODYSPLASIA PUNCTATA 1, XLR RECESSIVE; CDPX1 | ARSE | 302950 |
| CHOROIDEREMIA; CHM | CHM | 303100 |
| MASA SYNDROME | L1CAM | 303350 |
| CORPUS CALLOSUM, PARTIAL AGENESIS OF, XLR | L1CAM | 304100 |
| IMMUNODYSREGULATION, POLYENDOCRINOPATHY, AND ENTEROPATHY, XLR | FOXP3 | 304790 |
| ECTODERMAL DYSPLASIA, HYPOHIDROTIC, XLR; XHED | EDA | 305100 |
| GLUCOSE-6-PHOSPHATE DEHYDROGENASE; G6PD | G6PD | 305900 |
| HETEROTAXY, VISCERAL, 1, XLR; HTX1 | ZIC3 | 306955 |
| HYDROCEPHALUS DUE TO CONGENITAL STENOSIS OF AQUEDUCT OF SYLVIUS; HSAS | L1CAM | 307000 |
| IMMUNODEFICIENCY WITH HYPER-IgM, 1; HIGM1 | CD40LG | 308230 |
| LYMPHOPROLIFERATIVE SYNDROME, XLR, 1; XLP1 | SH2D1A | 308240 |
| EPILEPTIC ENCEPHALOPATHY, EARLY INFANTILE, 1 | ARX | 308350 |
| INFERTILE MALE SYNDROME | AR | 308370 |
| LEIGH SYNDROME, XLR | PDHA1 | 308930 |
| LOWE OCULOCEREBRORENAL SYNDROME; OCRL | OCRL | 309000 |
| MENKES DISEASE | ATP7A | 309400 |
| RENPENNING SYNDROME 1; RENS1 | PQBP1 | 309500 |
| LUJAN-FRYNS SYNDROME | MED12 | 309520 |
| MUSCULAR DYSTROPHY, DUCHENNE ; DMD | DMD | 310200 |
| MYOTUBULAR MYOPATHY 1; MTM1 | MTM1 | 310400 |
| NORRIE DISEASE; ND | NDP | 310600 |
| OPTICOACOUSTIC NERVE ATROPHY WITH DEMENTIA | TIMM8A | 311150 |
| ORNITHINE TRANSCARBAMYLASE DEFICIENCY, HYPERAMMONEMIA DUE TO | OTC | 311250 |
| PROPERDIN DEFICIENCY, XLR | CFP | 312060 |
| PELIZAEUS-MERZBACHER DISEASE; PMD | PLP1 | 312080 |
| RETINOSCHISIS 1, XLR, JUVENILE; RS1 | RS1 | 312700 |
| RETT SYNDROME; RTT | MECP2 | 312750 |
| COMBINED IMMUNODEFICIENCY, XLR; CIDX | IL2RG | 312863 |
| SPASTIC PARAPLEGIA 2, XLR; SPG2 | PLP1 | 312920 |
| VACTERL ASSOCIATION WITH HYDROCEPHALUS, XLR | FANCB | 314390 |
| DEAFNESS, NEUROSENSORY, AR 2; DFNB2 | MYO7A | 600060 |
| WARBURG MICRO SYNDROME; WARBM | RAB3GAP1 | 600118 |

Fig. 8 cont.

| DISEASE | GENE | OMIM# |
|---|---|---|
| RHIZOMELIC CHONDRODYSPLASIA PUNCTATA, 3; RCDP3 | AGPS | 600121 |
| CEROID LIPOFUSCINOSIS, NEURONAL, 8; CLN8 | CLN8 | 600143 |
| ABCD SYNDROME | EDNRB | 600501 |
| CARNITINE PALMITOYLTRANSFERASE II DEFICIENCY, INFANTILE | CPT2 | 600649 |
| D-2-HYDROXYGLUTARIC ACIDURIA | D2HGDH | 600721 |
| INCLUSION BODY MYOPATHY 2, AR; IBM2 | GNE | 600737 |
| SEVERE COMBINED IMMUNODEFICIENCY, AR, T CELL- B CELL+, NK CELL- | JAK3 | 600802 |
| ACHONDROGENESIS, IB; ACG1B | SLC26A2 | 600972 |
| USHER SYNDROME, ID; USH1D | CDH23 | 601067 |
| MICROPHTHALMIA, SYNDROMIC 9; MCOPS9 | STRA6 | 601186 |
| CRISPONI SYNDROME | CRLF1 | 601378 |
| NEVO SYNDROME | PLOD1 | 601451 |
| SEVERE COMBINED IMMUNODEFICIENCY, AR, T CELL-NEGATIVE, | RAG1 | 601457 |
| SEVERE COMBINED IMMUNODEFICIENCY, AR, T CELL-NEGATIVE, | RAG2 | 601457 |
| STUVE-WIEDEMANN SYNDROME | LIFR | 601559 |
| TRICHOTHIODYSTROPHY, PHOTOSENSITIVE; TTDP | ERCC2 | 601675 |
| TRICHOTHIODYSTROPHY, PHOTOSENSITIVE; TTDP | ERCC3 | 601675 |
| TRICHOTHIODYSTROPHY, PHOTOSENSITIVE; TTDP | GTF2H5 | 601675 |
| BARTTER SYNDROME, ANTENATAL, 1 | SLC12A1 | 601678 |
| T-CELL IMMUNODEFICIENCY, CONGENITAL ALOPECIA, AND NAIL DYSTROPHY | FOXN1 | 601705 |
| YEMENITE DEAF-BLIND HYPOPIGMENTATION SYNDROME | SOX10 | 601706 |
| CEROID LIPOFUSCINOSIS, NEURONAL, 6; CLN6 | CLN6 | 601780 |
| CHOLESTASIS, PROGRESSIVE FAMILIAL INTRAHEPATIC 2; PFIC2 | ABCB11 | 601847 |
| USHER SYNDROME, IF; USH1F | PCDH15 | 602083 |
| NEPHRONOPHTHISIS 2; NPHP2 | INVS | 602088 |
| HEMOCHROMATOSIS, JUVENILE; JH | HAMP | 602390 |
| HEMOCHROMATOSIS, JUVENILE; JH | HFE2 | 602390 |
| DESMOSTEROLOSIS | DHCR24 | 602398 |
| ENCEPHALOPATHY, ETHYLMALONIC | ETHE1 | 602473 |
| CONGENITAL DISORDER OF GLYCOSYLATION, Ib; CDG1B | MPI | 602579 |
| RIGID SPINE MUSCULAR DYSTROPHY 1; RSMD1 | SEPN1 | 602771 |
| CONGENITAL DISORDER OF GLYCOSYLATION, Ic; CDG1C | ALG6 | 603147 |
| GRACILE SYNDROME | BCS1L | 603358 |
| OMENN SYNDROME | DCLRE1C | 603554 |
| OMENN SYNDROME | RAG1 | 603554 |
| OMENN SYNDROME | RAG2 | 603554 |
| CONGENITAL DISORDER OF GLYCOSYLATION, IIf; CDG2F | SLC35A1 | 603585 |
| SICKLE CELL ANEMIA | HBB | 603903 |
| MEGALENCEPHALIC LEUKOENCEPHALOPATHY WITH SUBCORTICAL CYSTS; MLC | MLC1 | 604004 |
| HEMOCHROMATOSIS, 3 | TFR2 | 604250 |
| SPINAL MUSCULAR ATROPHY, DISTAL, AR, 1; DSMA1 | IGHMBP2 | 604320 |
| SIALURIA, FINNISH | SLC17A5 | 604369 |

Fig. 8 cont.

| DISEASE | GENE | OMIM# |
|---|---|---|
| CARDIOENCEPHALOMYOPATHY, FATAL INFANTILE, DUE TO CYTOCHROME c OXIDASE | SCO2 | 604377 |
| AMEGAKARYOCYTIC THROMBOCYTOPENIA, CONGENITAL; CAMT | MPL | 604498 |
| C-LIKE SYNDROME | CD96 | 605039 |
| NEUROPATHY, HYPOMYELINATING/CHARCOT-MARIE-TOOTH DISEASE, 4E | EGR2 | 605253 |
| NEUROPATHY, HYPOMYELINATING/CHARCOT-MARIE-TOOTH DISEASE, 4E | MPZ | 605253 |
| NEMALINE MYOPATHY 5; NEM5 | TNNT1 | 605355 |
| SEGAWA SYNDROME, AR | TH | 605407 |
| USHER SYNDROME, IIC; USH2C | GPR98 | 605472 |
| GLYCINE ENCEPHALOPATHY; GCE | AMT | 605899 |
| GLYCINE ENCEPHALOPATHY; GCE | GCSH | 605899 |
| GLYCINE ENCEPHALOPATHY; GCE | GLDC | 605899 |
| CONGENITAL DISORDER OF GLYCOSYLATION, IIb; CDG2B | MOGS | 606056 |
| PRIMARY LATERAL SCLEROSIS, JUVENILE; PLSJ | ALS2 | 606353 |
| EPILEPTIC ENCEPHALOPATHY, LENNOX-GASTAUT | MAPK10 | 606369 |
| HYPOTONIA-CYSTINURIA SYNDROME | PREPL | 606407 |
| HYPOTONIA-CYSTINURIA SYNDROME | SLC3A1 | 606407 |
| MUSCULAR DYSTROPY, CONGENITAL, 1C; MDC1C | FKRP | 606612 |
| FUMARASE DEFICIENCY | FH | 606812 |
| USHER SYNDROME, IG; USH1G | USH1G | 606943 |
| NEPHRONOPHTHISIS 4; NPHP4 | NPHP4 | 606966 |
| HURLER SYNDROME | IDUA | 607014 |
| CONGENITAL DISORDER OF GLYCOSYLATION, IId; CDG2D | B4GALT1 | 607091 |
| ANAUXETIC DYSPLASIA | RMRP | 607095 |
| LATHOSTEROLOSIS | SC5DL | 607330 |
| COENZYME Q10 DEFICIENCY | APTX | 607426 |
| COENZYME Q10 DEFICIENCY | CABC1 | 607426 |
| COENZYME Q10 DEFICIENCY | COQ2 | 607426 |
| COENZYME Q10 DEFICIENCY | PDSS1 | 607426 |
| COENZYME Q10 DEFICIENCY | PDSS2 | 607426 |
| ICOS DEFICIENCY; LCCS2 | ERBB3 | 607598 |
| NIEMANN-PICK DISEASE, B | SMPD1 | 607616 |
| GRISCELLI SYNDROME, 2; GS2 | RAB27A | 607624 |
| NIEMANN-PICK DISEASE, C2 | NPC2 | 607625 |
| ICHTHYOSIS, LEUKOCYTE VACUOLES, ALOPECIA, AND SCLEROSING CHOLANGITIS | CLDN1 | 607626 |
| SKIN FRAGILITY-WOOLLY HAIR SYNDROME | DSP | 607655 |
| MUSCULAR DYSTROPHY, CONGENITAL MEROSIN-DEFICIENT, 1A; MDC1A | LAMA2 | 607855 |
| GAUCHER DISEASE, PERINATAL LETHAL | GBA | 608013 |
| CONGENITAL DISORDER OF GLYCOSYLATION, Ij; CDG1J | DPAGT1 | 608093 |
| MUSCULAR DYSTROPHY, LIMB-GIRDLE, 2D; LGMD2D | SGCA | 608099 |
| COLORECTAL ADENOMATOUS POLYPOSIS, AR | MUTYH | 608456 |
| CONGENITAL DISORDER OF GLYCOSYLATION, Ik; CDG1K | ALG1 | 608540 |
| MANDIBULOACRAL DYSPLASIA WITH B LIPODYSTROPHY; MADB | ZMPSTE24 | 608612 |

Fig. 8 cont.

| DISEASE | GENE | OMIM# |
|---|---|---|
| JOUBERT SYNDROME 3; JBTS3 | AHI1 | 608629 |
| AROMATIC L-AMINO ACID DECARBOXYLASE DEFICIENCY | DDC | 608643 |
| AICAR TRANSYLASE/IMP CYCLOHYDROLASE, DEFICIENCY OF | ATIC | 608688 |
| PYRUVATE DEHYDROGENASE PHOSPHATASE DEFICIENCY | PDP1 | 608782 |
| CONGENITAL DISORDER OF GLYCOSYLATION, Ie; CDG1E | DPM1 | 608799 |
| SUDDEN INFANT DEATH WITH DYSGENESIS OF THE TESTES SYNDROME; SIDDT | TSPYL1 | 608800 |
| LEUKODYSTROPHY, HYPOMYELINATING, 2 | GJC2 | 608804 |
| CARNITINE PALMITOYLTRANSFERASE II DEFICIENCY, LETHAL NEONATAL | CPT2 | 608836 |
| MUSCULAR DYSTROPHY, CONGENITAL, 1D | LARGE | 608840 |
| TRIFUNCTIONAL PROTEIN DEFICIENCY | HADHA | 609015 |
| TRIFUNCTIONAL PROTEIN DEFICIENCY | HADHB | 609015 |
| LONG-CHAIN 3-HYDROXYACYL-CoA DEHYDROGENASE DEFICIENCY | HADHA | 609016 |
| PIERSON SYNDROME | LAMB2 | 609049 |
| AMISH INFANTILE EPILEPSY SYNDROME | ST3GAL5 | 609056 |
| COMBINED OXIDATIVE PHOSPHORYLATION DEFICIENCY 1; COXPD1 | GFM1 | 609060 |
| SCHINDLER DISEASE, I | NAGA | 609241 |
| SENIOR-LOKEN SYNDROME 5; SLSN5 | IQCB1 | 609254 |
| EPILEPTIC ENCEPHALOPATHY, EARLY INFANTILE, 3 | SLC25A22 | 609304 |
| CHARCOT-MARIE-TOOTH DISEASE, 4H; CMT4H | FGD4 | 609311 |
| CEREBRAL DYSGENESIS, NEUROPATHY, ICHTHYOSIS, PALMOPLANTAR KERATODERMA | SNAP29 | 609528 |
| MITOCHONDRIAL DNA DEPLETION SYNDROME, MYOPATHIC | TK2 | 609560 |
| JOUBERT SYNDROME 4; JBTS4 | NPHP1 | 609583 |
| EPIDERMOLYSIS BULLOSA, LETHAL ACANTHOLYTIC | DSP | 609638 |
| CEROID LIPOFUSCINOSIS, NEURONAL, 8, NORTHERN EPILEPSY | CLN8 | 610003 |
| 2-METHYLBUTYRYL-CoA DEHYDROGENASE DEFICIENCY | ACADSB | 610006 |
| PYRIDOXAMINE 5-PRIME-PHOSPHATE OXIDASE DEFICIENCY | PNPO | 610090 |
| CEROID LIPOFUSCINOSIS, NEURONAL, 10; CLN10 | CTSD | 610127 |
| JOUBERT SYNDROME 5; JBTS5 | CEP290 | 610188 |
| 3-METHYLGLUTACONIC ACIDURIA, V | DNAJC19 | 610198 |
| DIARRHEA 4, MALABSORPTIVE, CONGENITAL | NEUROG3 | 610370 |
| MEVALONIC ACIDURIA | MVK | 610377 |
| COMBINED OXIDATIVE PHOSPHORYLATION DEFICIENCY 2; COXPD2 | MRPS16 | 610498 |
| COMBINED OXIDATIVE PHOSPHORYLATION DEFICIENCY 3; COXPD3 | TSFM | 610505 |
| LEUKODYSTROPHY, HYPOMYELINATING, 5 | FAM126A | 610532 |
| XERODERMA PIGMENTOSUM, COMPLEMENTATION GROUP B; XPB | ERCC3 | 610651 |
| JOUBERT SYNDROME 6; JBTS6 | TMEM67 | 610688 |
| NEPHROTIC SYNDROME, 3; NPHS3 | PLCE1 | 610725 |

Fig. 8 cont.

| DISEASE | GENE | OMIM# |
|---|---|---|
| CONGENITAL DISORDER OF GLYCOSYLATION, Im; CDG1M | DOLK | 610768 |
| OSTEOGENESIS IMPERFECTA, IIB | CRTAP | 610854 |
| OSTEOGENESIS IMPERFECTA, VIII | LEPRE1 | 610915 |
| CEROID LIPOFUSCINOSIS, NEURONAL, 7; CLN7 | MFSD8 | 610951 |
| PHOSPHOSERINE AMINOTRANSFERASE DEFICIENCY | PSAT1 | 610992 |
| SPINAL MUSCULAR ATROPHY, DISTAL, AR, 4; DSMA4 | PLEKHG5 | 611067 |
| ACYL-CoA DEHYDROGENASE FAMILY, MEMBER 9, DEFICIENCY OF | ACAD9 | 611126 |
| MECKEL SYNDROME, 5; MKS5 | RPGRIP1L | 611561 |
| MYOPATHY, EARLY-ONSET, WITH FATAL CARDIOMYOPATHY | TTN | 611705 |
| COMBINED OXIDATIVE PHOSPHORYLATION DEFICIENCY 5; COXPD5 | MRPS22 | 611719 |
| COMBINED SAPOSIN DEFICIENCY | PSAP | 611721 |
| KRABBE DISEASE, ATYPICAL, DUE TO SAPOSIN A DEFICIENCY | PSAP | 611722 |
| EPILEPSY, PROGRESSIVE MYOCLONIC 3; EPM3 | KCTD7 | 611726 |
| EPILEPTIC ENCEPHALOPATHY, EARLY INFANTILE, 4 | STXBP1 | 612164 |
| THROMBOPHILIA, HEREDITARY, DUE TO PROTEIN C DEFICIENCY, AUTOSOMAL | PROC | 612304 |
| FACTOR XI DEFICIENCY | F11 | 612416 |

Fig. 8 cont.

SYSTEM AND METHOD FOR THE COMPUTATIONAL PREDICTION OF EXPRESSION OF SINGLE-GENE PHENOTYPES

CROSS-REFERENCE TO RELATED APPLICATIONS

This application is a National Phase Application of PCT International Application No. PCT/US13/73415, International Filing Date Dec. 5, 2013, claiming priority to U.S. Provisional Application Ser. No. 61/733,600, filed Dec. 5, 2012, which are incorporated herein by reference in their entirety.

FIELD OF EMBODIMENTS OF THE INVENTION

Embodiments of the present invention relate generally to the field of genetics. In particular, embodiments of the present invention relate to predicting expression of single gene phenotypes in virtual or potential progeny or to predicting a future emergence of expression of single gene phenotypes in living organisms.

Background of Embodiments of the Invention

Carrier testing is currently the most highly resolving method for determining the risk of recessive disease in a potential child of two prospective parents. A carrier test determines whether or not a potential parent has one gene copy containing a mutation associated with an autosomal recessive Mendelian disease caused by mutations in both copies of the gene. DNA-based carrier tests for over one thousand disease-genes have been defined, for example, at Genetic Testing Registry (GTR) at the National Center for Biotechnology Information (NCBI).

A "carrier" of a recessive disease mutation does not exhibit disease symptoms because that person also carries a "normal" allele of the gene that produces a sufficient amount of the protein. But when two individuals are both carriers for a recessive mutation in the same gene, the likelihood of having a child with the disease is 25%.

Carrier tests are designed and scored based on the simple Mendelian assumption that every variant of a gene is either "pathogenic" (mutant) or "non-pathogenic" (normal). As a consequence, carrier test results are restricted to one of three possible outcomes: a "positive" diagnosis means the variant is known empirically to be pathogenic; a "negative" diagnosis means the variant is known to be non-pathogenic; and "VUS" refers to a variant of unknown significance which means that a diagnosis cannot be made because of the lack of sufficient prior data. Still, the assumption is that VUS is a temporary classification and that with sufficient data, the variant will be classifiable as either positive (pathogenic) or negative (non-pathogenic).

Reference is made to FIG. 1, which is a diagram of traditional carrier testing results for (n=4) variants of the ACYL-CoA Dehydrogenase Medium-Chain (ACADM) gene associated with the genetic disease MCADD. The table in FIG. 1 charts the ($n^2$=16) possible combinations of such variants in a potential progeny of maternal and paternal parents. Tests are positive for MCADD expression in the potential progeny when the combined proportional reduction in function of the maternal and paternal parents is above a threshold and negative when the combined proportional reduction in function is below a threshold. The simple positive/negative results do not distinguish between mild and severe forms of the disease. The carrier test also provides a number of inaccurate diagnoses in the form of false positives and false negatives as compared to the validated clinical outcome results empirically observed that are shown in FIG. 2.

Carrier testing is unique among diagnostic tests in that disease is typically only observed in persons other than those being tested. This is problematic for several reasons. First, a positive diagnosis has no disease relevance to a person who chooses not to reproduce. Second, even for cystic fibrosis (CF: the most prevalent serious recessive disease among children born to people of European descent), the risk of disease for a child of a diagnosed carrier is only 1%. (In northern European populations, the carrier frequency for pathogenic mutations in the cystic fibrosis-associated CFTR gene is 0.04, which represents the probability (4%) that a diagnosed carrier will, by chance, many another carrier. The probability that a child of two carriers will inherit the disease is 25%. Thus, the next-generation risk to a single person who is a CF carrier is 0.04×0.25=0.01 or 1%.) Nevertheless, if the simple Mendelian model of disease causation were true and two prospective parents both tested positive, the result would be sufficient to predict a 25% risk of disease in their child.

However, the Mendelian model is not correct in many cases, for example, because a gene may harbor variants at any DNA base across its coding region. Different non-synonymous variants may correspond to different amino acid changes at different locations in the gene product with different effects on protein function. Whether a child expresses a phenotype such as disease, and how severely, may depend on the particular pair of variants present in a genotype. In particular, the same variant may cause severe disease in genotypic combination with some variants but not others. In such cases, simple categorization of a variant as pathogenic or non-pathogenic is meaningless, as is the notion of carrier status.

Carrier tests are typically categorized as medical diagnostic tests and, as such, typically undergo the same process of validation as other diagnostic tests. Reference is made to FIG. 2, which is a diagram of validated clinical outcome results for the variants of the ACADM gene shown in FIG. 1. Validation requires a demonstrated association between test results and clinical disease. This means that a particular DNA variant cannot be considered pathogenic unless it is found in a child with disease. In the pre-personal genomics era (prior to 2007), pathogenic variants were routinely discovered through DNA sequencing of children expressing disease. However, with whole exome sequencing of tens of thousands of healthy individuals, numerous supposedly pathogenic DNA variants have been discovered in known disease genes without having been observed in subjects.

The lack of forward association is not unexpected since the incidence of a recessive disease is typically orders of magnitude lower than the frequency of corresponding disease alleles. As an example, a genetic disease with an incidence of one in 40,000 is associated with a carrier frequency of 1% (according to a Hardy-Weinberg calculation). In the absence of disease association, a particular damaging DNA variant may not be incorporated into a "diagnostic" carrier test, even if disease likelihood may be estimated on theoretical grounds. As a consequence of large-scale sequencing efforts, unvalidated but potentially deleterious DNA variants (in the VUS class) now outnumber validated disease variants in nearly every established recessive disease gene. Thus, the {+/−/VUS} result choice used in diagnostic testing is even less accurate in predicting gene expression in virtual progeny since there may be no clinical validation of a simulated organism.

Summary of Embodiments of the Invention

There is now provided according to embodiments of the invention an improved system and method for effectively overcoming the aforementioned difficulties inherent in the fields of carrier testing and clinical validation.

In accordance with an embodiment of the invention, a system and method is provided for determining a probability of a progeny having one or more phenotypes $Ph_j$ each associated with a single gene $Q_j$. A haplopath $H^p = \{h_1^p, h_1^p, \ldots, h_N^p\}$ may be generated including a single allele $h_i^p \in (1,2)$ at each of a plurality of loci (i=1, ..., N) from a genome profile of a potential parent (p). A variance score $s_i^p$ may be assigned to each of a plurality of the alleles $h_i^p$ in the haplopath. Each of the variance scores $s_i^p$ may indicate a probability that the allele $h_i^p$ results in altering the gene product from gene $Q_j$. Each variant allele $h_i^{p1}$, which has a variance score $s_i^p$ indicating a non-zero probability, may be associated with a corresponding one of a plurality of (k=1, ..., Nj) variant alleles $h_k^p$ known to alter the gene product from gene $Q_j$. For each gene $Q_j$, a gene-specific penetrance score $\hat{s}_{j,k}^p$ may be assigned to each of the (Nj) variant alleles $h_k^p$ associated with the gene $Q_j$. For each gene $Q_j$, a probability of altering the gene product from gene $Q_j$ in the virtual progeny of the parent (p) may be determined based on the gene-specific penetrance scores $\hat{s}_{j,k}^p$ of the plurality of (Nj) variant alleles $h_k^p$. For each gene $Q_j$, the probability of expression of the phenotype $Ph_j$ or a derivation of the probability of altering the gene product or a derivation of the probability of altering the gene product, for example, displayed or further processed.

In accordance with an embodiment of the invention, a system and method is provided for determining a probability of a progeny having one or more phenotypes $Ph_j$ each associated with a single gene $Q_j$. A score $s_i^p$ may be assigned to each allele $h_i^p$ at a plurality of genetic loci (i) in a haploid genome profile $H^p$ of a parent (p). A plurality (Nj) of the alleles $h_k^p$ (k=1, ..., Nj) associated with the gene $Q_j$ may be identified. The scores $s_i^p$ may be mapped or indexed to gene-specific scores $\hat{s}_{j,k}^p$ associated with gene $Q_j$ for the plurality of (Nj) alleles $h_k^p$. A probability of altering gene product from gene $Q_j$ in a progeny of the parent (p) may be computed to be a function of the gene-specific scores $\hat{s}_{j,k}^p$.

In accordance with an embodiment of the invention, a system and method is provided for determining a probability of having a phenotype in a virtual progeny. A virtual progeny genome sampling G may be generated, wherein at each of a plurality of genetic loci i=1, ..., N the sampling comprises one allele $h_i^{p1}$ from a first genome profile of a first potential parent (p1) and one allele $h_i^{p2}$ from a second genome profile of a second potential parent (p2). Genotypes of said virtual progeny genome sampling G may be compared to one or more databases of genotype-phenotype associations to determine a phenotype associated with database genotypes matching genotypes of said virtual progeny genome sampling G. Each genotype-phenotype association may also be associated with a penetrance value. A random number may be generated to determine if the virtual progeny is predicted to express the phenotype. If the virtual progeny is predicted to express the phenotype, the penetrance value may be associated with a degree of expressivity of the phenotype in the virtual progeny.

In contrast to current methods that consider only a positive/negative (or unknown, VUS) carrier status for individual persons, embodiments of the invention provide a scale of the degree or severity of expression in actual or simulated genomes. In contrast to current methods that assume a 100% correlation between genotype and phenotype, embodiments of the invention generate a random number to randomize the correlation between genotype and phenotype that mimics the randomized correlation in nature. In contrast to current methods that score phenotypic expression for each allele individually, embodiments of the invention combining gene-specific scores for a plurality of alleles associated with a gene, thereby incorporating all possible gene-specific effects.

BRIEF DESCRIPTION OF THE DRAWINGS

The subject matter regarded as the invention is particularly pointed out and distinctly claimed in the concluding portion of the specification. The invention, however, both as to organization and method of operation, together with objects, features, and advantages thereof, may best be understood by reference to the following detailed description when read with the accompanying drawings in which:

FIG. 8 lists genes and their associated diseases, which may be used for computer-generated diagnosis according to embodiments of the invention.

Figure 1:
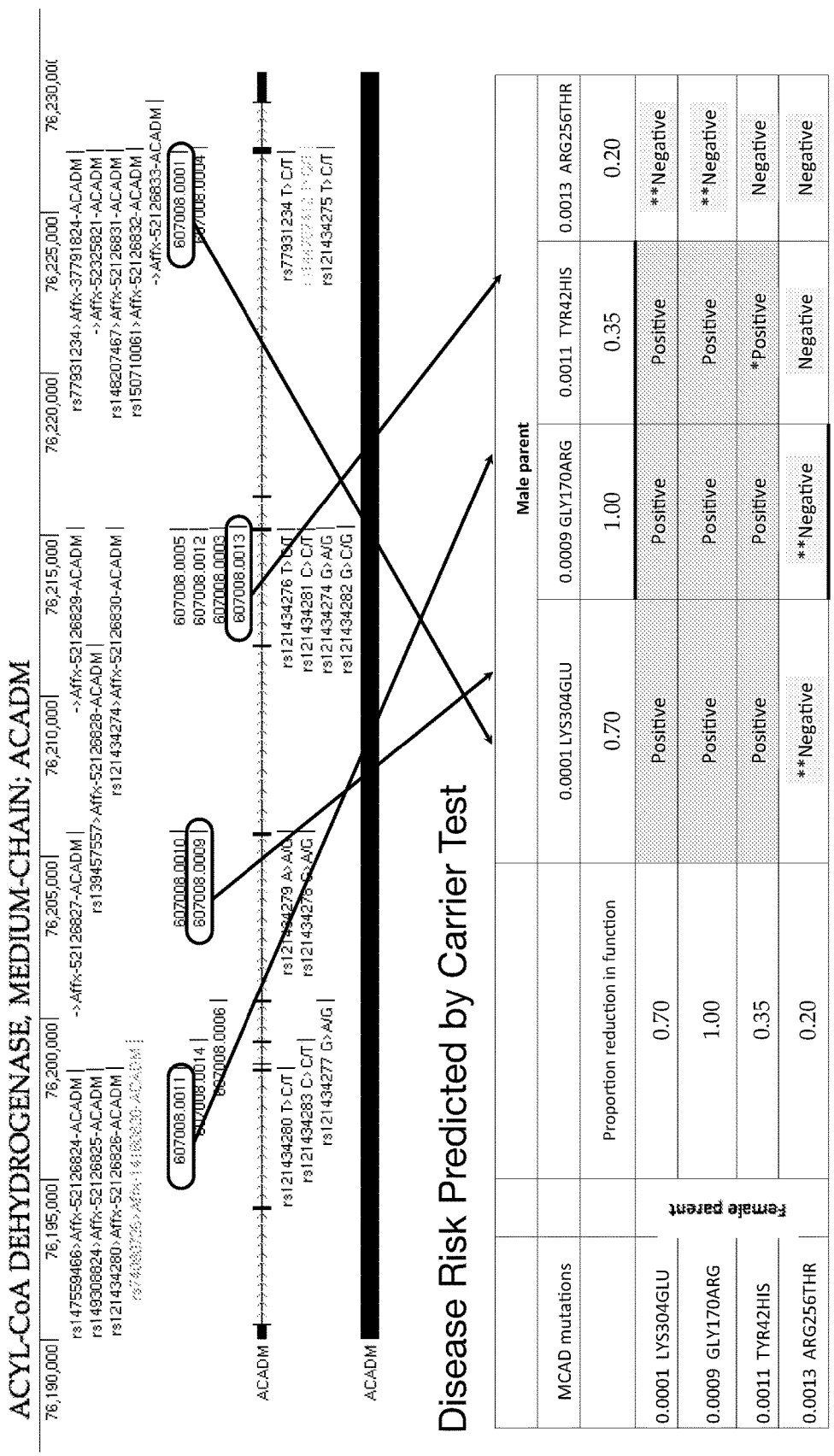
FIG. 1 is a diagram of traditional carrier testing results for variants of the ACYL-CoA Dehydrogenase Medium-Chain (ACADM) gene associated with the genetic disease MCAD deficiency.
Figure 2:
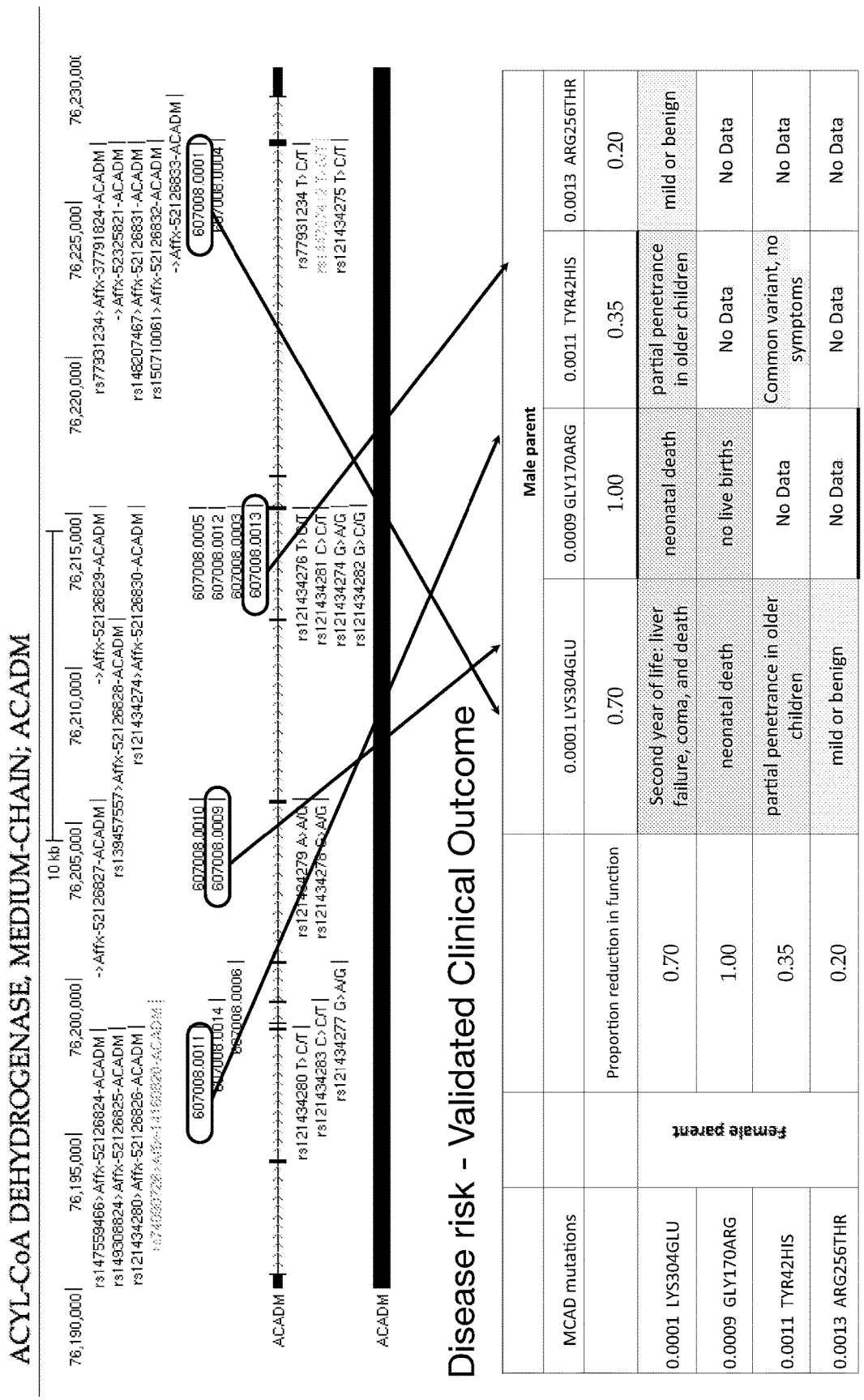
FIG. 2 is a diagram of validated clinical outcome results for the variants of the ACADM gene shown in FIG. 1.

It will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements.

DETAILED DESCRIPTION OF EMBODIMENTS OF THE INVENTION

In the following description, various aspects of the present invention will be described. For purposes of explanation, specific configurations and details are set forth in order to provide a thorough understanding of the present invention. However, it will also be apparent to one skilled in the art that the present invention may be practiced without the specific details presented herein. Furthermore, well known features may be omitted or simplified in order not to obscure the present invention.

Unless specifically stated otherwise, as apparent from the following discussions, it is appreciated that throughout the specification discussions utilizing terms such as "processing," "computing," "calculating," "determining," or the like, refer to the action and/or processes of a computer or computing system, or similar electronic computing device, that manipulates and/or transforms data represented as physical, such as electronic, quantities within the computing system's registers and/or memories into other data similarly represented as physical quantities within the computing system's memories, registers or other such information storage, transmission or display devices.

In accordance with embodiments of the present invention and as used herein, the following terms are defined with the following meanings, unless explicitly stated otherwise.

As used herein, "haploid cell" refers to a cell with a haploid number (n) of chromosomes.

"Gametes", as used herein, are specialized haploid cells (e.g., spermatozoa and oocytes) produced through the process of meiosis and involved in sexual reproduction.

As used herein, "gametotype" refers to single genome copies with one allele of each of one or more loci in the haploid genome of a single gamete.

As used herein, an "autosome" is any chromosome exclusive of the X and Y sex chromosomes.

As used herein, "diploid cell" has a homologous pair of each of its autosomal chromosomes, and has two copies (2n) of each autosomal genetic locus.

The term "chromosome", as used herein, refers to a molecule of DNA with a sequence of base pairs that corresponds closely to a defined chromosome reference sequence of the organism in question.

The term "gene", as used herein, refers to a DNA sequence in a chromosome that codes for a product (either RNA or its translation product, a polypeptide) or otherwise plays a role in the expression of said product. A gene contains a DNA sequence with biological function. The biological function may be contained within the structure of the RNA product or a coding region for a polypeptide. The coding region includes a plurality of coding segments ("exons") and intervening non-coding sequences ("introns") between individual coding segments and non-coding regions preceding and following the first and last coding regions respectively.

The term "gene product", as used herein, refers to a product (either RNA or its translation product, a polypeptide) that is encoded by a gene and that has biological function.

As used herein, "locus" refers to any segment of DNA sequence defined by chromosomal coordinates in a reference genome known to the art, irrespective of biological function. A DNA locus may contain multiple genes or no genes; it may be a single base pair or millions of base pairs.

As used herein, a "polymorphic locus" is a genomic locus at which two or more alleles have been identified.

As used herein, an "allele" is one of two or more existing genetic variants of a specific polymorphic genomic locus.

As used herein, a "single nucleotide polymorphism" or "SNP" is a particular base position in the genome where alternative bases are known to distinguish one individual from another. Most categories of more complex genetic variants may be reduced for analytical purposes to one or a few defining SNPs.

As used herein, a "copy number variant" or "CNV" is a deletion or duplication of a large block of genetic material that exists in a population at a frequency less than 1%.

As used herein, a "copy number polymorphism" or "CNP" is a deletion or duplication of a large block of genetic material that exists in a population at a frequency of greater than 1%. Since a CNV in one population may be a CNP in a second population, the two terms may be used interchangeably.

As used herein, "genotype" refers to the diploid combination of alleles at a given genetic locus, or set of related loci, in a given cell or organism. A homozygous subject carries two copies of the same allele and a heterozygous subject carries two distinct alleles. In the simplest case of a locus with two alleles "A" and "a", three genotypes may be formed: A/A, A/a, and a/a.

As used herein, "genotyping" refers to any experimental, computational, or observational protocol for distinguishing an individual's genotype at one or more well-defined loci.

As used herein, a "haplotype" is a unique set of alleles at separate loci that are normally grouped closely together on the same DNA molecule, and are observed to be inherited as a group. A haplotype may be defined by a set of specific alleles at each defined polymorphic locus within a haploblock.

As used herein, a "haploblock" refers to a genomic region that maintains genetic integrity over multiple generations and is recognized by linkage disequilibrium within a population. Haploblocks are defined empirically for a given population of individuals.

As used herein, "linkage disequilibrium" is the non-random association of alleles at two or more loci within a particular population. Linkage disequilibrium is measured as a departure from the null hypothesis of linkage equilibrium, where each allele at one locus associates randomly with each allele at a second locus in a population of individual genomes.

As used herein, a "genome" is the total genetic information carried by an individual organism or cell, represented by the complete DNA sequences of its chromosomes.

As used herein, a "genome profile" is a representative subset of the total information contained within a genome. A genome profile contains genotypes at a particular set of polymorphic loci.

As used herein, a "personal genome profile", abbreviated PGP, is the genome profile of a particular individual person.

As used herein, a genetic "trait" is a distinguishing attribute of an individual, whose expression is fully or partially influenced by an individual's genetic constitution.

As used herein, "disease" refers to a trait that is at least partially heritable and causes a reduction in the quality of life of an individual person.

As used herein, a "phenotype" includes alternative traits which may be discrete or continuous. Phenotypes may include both traits and diseases.

As used herein, a "haplopath" is a haploid path laid out along a defined region of a diploid genome by a single iteration of a Monte Carlo simulation or a single chain generated through a Markov process. A haplopath is generated through the application of formal rules of genetics that describe the reduction of the diploid genome into haploid genomes through the natural process of meiosis. It may be formed by starting at one end of a personal chromosome or genome and walking from locus to locus, choosing a single allele at each step based on available linkage disequilibrium information, inter-locus allele association coefficients, and formal rules of genetics that describe the natural process of gamete production in a sexually reproducing organism.

A Virtual Gamete is a single haplopath that extends across an entire genome.

As used herein, a "Virtual Progeny genome sampling" is the discrete genetic product of two Virtual Gametes.

As used herein, a "Virtual Progeny genome" is a collection of discrete Virtual Progeny genome samplings, each generated by combining two uniquely-derived (e.g. random or partially random) Virtual Gametes. In some instances, a Virtual Progeny genome is represented as a probability mass function over a sample space of all discrete genome states. In some instances, a Virtual Progeny genome is an informed simulation of a child or children that might result as a consequence of sexual reproduction between two individuals.

As used herein, a "Virtual Progeny phenome" is a multi-dimensional likelihood function representing the likelihood and/or likely degree of expression of a set of one or more phenotypes from a complete Virtual Progeny genome. In some instances, a Virtual Progeny phenome is represented as a probability mass function over a sample space of discrete or continuous phenotypic states. In some instances, a Virtual Progeny phenome is an informed simulation of a child or children that might result as a consequence of sexual reproduction between two individuals.

As used herein, "partner" includes a marriage partner, sexual or reproductive partner, domestic partner, opposite-sex partner, and same-sex partner.

The methods and compositions disclosed herein relate to assessing the genotypes of individuals and the phenotypes associated with particular genotypes of potential progeny from such individuals. Generally, genome profiles from two individuals are used to determine the probabilities that potential progeny from such individuals will express certain traits, such as an increased risk of disease. Such methods are referred to herein as "Virtual Progeny assessment."

As used herein, "NCBI" refers to the National Center for Biotechnology Information which is a division of the National Library of Medicine at the U.S. National Institutes of Health. The NCBI operates under a Congressional mandate to develop, maintain and distribute databases and software to the research and medical communities.

As used herein, a "variant" is a particular allele at a locus where at least two alleles have been identified.

As used herein, a "mutation" has the same meaning as a "mutant allele" which is a variant that causes a gene to function abnormally.

As used herein, a "single gene phenotype" is a phenotype that may be caused by the expression of a genotype of a single gene.

As used herein, a "single gene disease" is a disease that may be caused by a mutation or mutations in a single gene As used herein, a "recessive phenotype" is a single gene phenotype whose expression is restricted to individuals who inherit a genotype with two copies of a particular gene.

As used herein, a "dominant phenotype" is a single gene phenotype whose expression is restricted to individuals who inherit a genotype with at least one copy of a particular gene.

As used herein, "disease risk" refers to the likelihood that an existing person or virtual progeny will express a specified disease based on an interpretation of genetic data which is informed by empirical data or bioinformatic modeling.

As used herein, a "non-synonymous variant" is a DNA variant that alters the coding sequence of a gene, thereby altering the amino acid sequence of the protein product of the gene.

As used herein, "altering the gene product" (and grammatical variations thereof and the like) from a gene, refers to a change of the wild-type or normal biological function of the gene and that is caused by mutations of the gene. Alteration of the gene product from a gene includes alterations to transcription of the gene, alterations to translation of the gene, and alterations to the gene product itself.

It may be appreciated by persons of skill in the art that the discussion herein of disease, mutations, variants and other defective or negative functions are only examples of phenotypes and that such embodiments relate to any phenotype having negative, positive or neutral function.

Embodiments of the invention may provide a system and method for testing for a probability of future emergence of phenotypes in living organisms (real progeny that do not currently express the phenotypes) or for testing for a probability of phenotypic expression in virtual progeny (simulated progeny or genetic information for a hypothetical organism that does not currently exist). Although a virtual progeny is not a living organism, its genetic information is derived or extracted from real genetic material of living organisms—the virtual progeny's living potential parents. (Living organisms may include organisms that were living at any time including those that are now dead.)

In contrast to a living organism that has known or empirically observable genetic information, the genetic information of a virtual progeny is unknown. To predict a virtual progeny genome sampling, a virtual haploid (e.g. a virtual sperm or egg) may be simulated from the real diploid genetic material of each potential parent. In nature, haploids are generated from diploids by genetic recombination in which two copies of a chromosome from a single parent are crossed or combined into one, e.g., at least partially at random.

Figure 4:
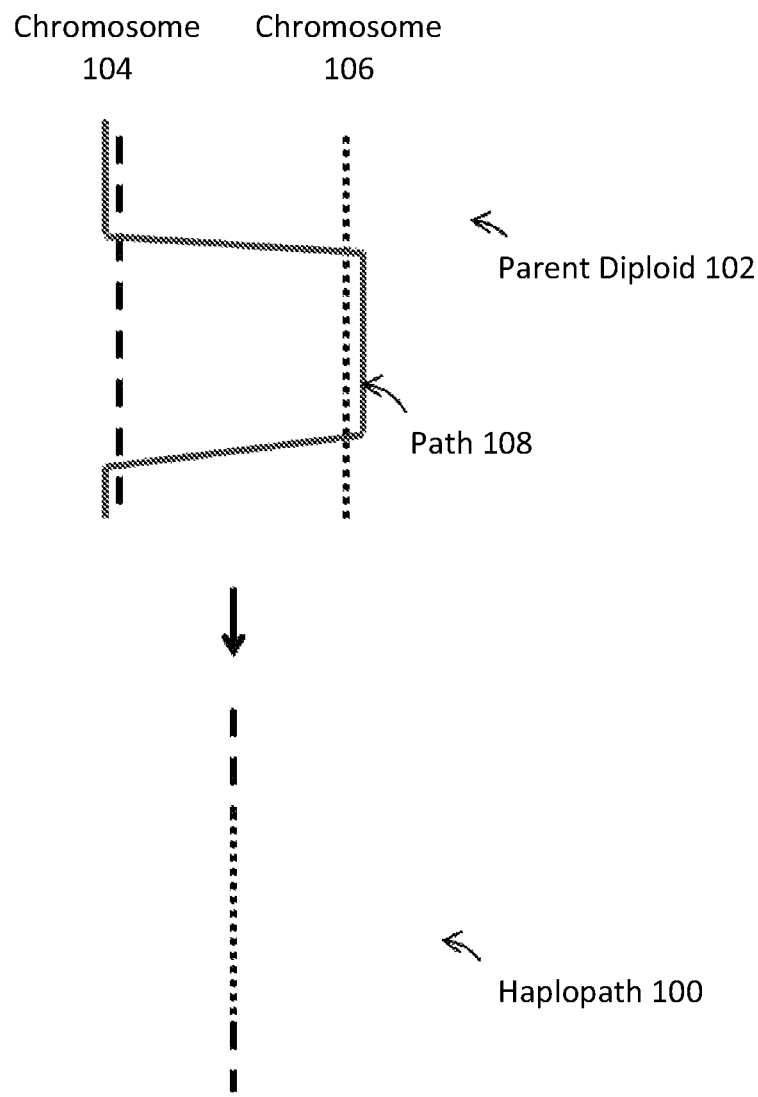
FIG. 4 is a schematic illustration of a haplopath or virtual gamete generated from a potential parent diploid genome profile according to an embodiment of the invention.

Reference is made to FIG. 4, which schematically illustrates a haplopath 100 generated from a potential parent diploid genome profile 102 in accordance with an embodiment of the invention. Haplopath 100 $H^p = \{h_1, h_2, \ldots, h_N\}$ may be a virtual gamete such as a virtual egg or virtual sperm (or genetic information therefrom) including a single allele $h_i \in (1,2)$ of a genotype at each of a plurality of loci i=1, ..., N from a diploid genome profile 102 of a potential parent (p). Generating the haplopath may simulate genetic recombination of the two chromosomes 104 and 106 from the parent's diploid genome profile 102 (having two alleles at each genetic locus) to generate one haploid or haplopath (having one allele per genetic locus). A haplopath may be generated by progressing locus-by-locus through the first parent's diploid genome and selecting one of the two alleles at each genetic locus (either the allele in chromosome 104 or the allele in chromosome 106). The process of selecting alleles locus-by-locus may resemble a path 108 moving or progressing back and forth between chromosomes 104 and 106. The selection of one allele per locus—a "haploid" progressing along that "path" 108—forms a virtual haploid referred to as a "haplopath" 100. Haplopath 100 may mimic virtual recombination of the genetic material in the two chromosomes 104 and 106 to form a discrete haploid genome, e.g., as a sperm or egg. This process may be repeated for each potential parent to generate two haplopaths 100 $H^{p1}$ and $H^{p2}$ (e.g. sperm and egg). The first and second haplopaths 100 may be combined to simulate the mating of the first and second potential parents resulting in a virtual progeny genome sampling $G = \{[h_i^{p1}, h_i^{p2}]; i=1, \ldots, N\}$ (a discrete genome of a child potentially to be conceived).

However, this mating is just one of the many possible genetic combinations of the first and second potential parents. To generate a statistically reliable result, this process is repeated multiple (M) times (e.g., a thousand or ten thousand times) to generate a virtual progeny genome G including a plurality of the virtual progeny genome samplings $G^{VP}=\{G_1, G_2, \ldots, G_M\}$, where each iteration may use a different genetic recombination path 108, to see other recombination possibilities of mating the first and second potential parents.

Phenotypic analysis may be executed for each individual virtual progeny sample G, and the results for all (or a subset) of the samplings in the virtual progeny $G^{VP}$ may be combined to generate an average probability, probability distribution or virtual progeny phenome (a multi-dimensional likelihood function) to indicate, for multiple possible simulated matings, the overall likelihood of phenotypic expression in a potential progeny.

Current carrier testing determines the probability of expression of a phenotype based each parent's allele at only a single genetic locus, one locus at a time (e.g. see the 16 individual +/− results for 16 individual mutant combinations for the two parents in FIG. 1). However, each phenotype $Ph_j$ and its corresponding gene $Qj$ may be associated with multiple (Nj) genetic loci (e.g. tens, hundreds or thousands). Any one (or combination of more than one) of the (Nj) gene-specific loci may activate (or damage) gene $Qj$ and trigger the expression of the corresponding phenotype $Ph_j$, and different combinations of the (Nj) gene-specific loci may trigger different degrees or likelihoods of expression. To take the multiple, gene-specific loci into account, embodiments of the invention may determine the probability of expression of phenotype $Ph_j$ by analyzing the impact of the combination of alleles at the plurality of the (Nj) associated gene-specific loci. Embodiments of the invention may test phenotype expression using a matching method and/or a scoring method.

In the matching method, genotypes from a virtual or real progeny genome sampling are compared and matched to one or more databases of genotype-phenotype associations. If database genotypes match the genotypes of the virtual progeny genome sampling at one, multiple or all of the (Nj) gene-specific loci, the progeny may have a non-zero probability of altering the gene product of gene $Q_j$. A random number may be generated and compared to one or more thresholds to predict if the virtual or living progeny will have the phenotype associated with the matched gene (e.g. an above-threshold random number indicating expression and a below-threshold random number indicating no expression). Determining phenotypic expression based on a random number may simulate the at least partially random correlation between genotype and phenotype expression in nature. If the phenotype is predicted to express, the degree or likelihood of expression may be defined as an expressivity or penetrance value (or a function thereof) associated with the matching genotype in the database. A match for a dominant gene may include a match of one of the two alleles for each genotype, while a match for a recessive gene may include only matches of both alleles for each genotype. When analyzing a living organism for recessive genotypes, each allele may be associated with its originating parent, for example, to detect if both parents carry an allele to express a recessive genotype.

In the scoring method, scores may be assigned to alleles at a plurality of genetic loci of each parent diploid genome profile. The scores may define a degree or likelihood of altering a gene product. The scores may be gene-specific, for example, representing an empirically observed or statistically predicted probability that alleles at the associated gene-specific genetic loci in the parents result in alteration of the gene product in a progeny of those parents, such as an autosomal recessive disease. In one example, there may be a mutation in which a damage score may indicate that an allele causes a loss of function of the gene product (e.g., alters the amino acid sequence known to damage the protein product of the gene causing a diseased phenotype). Scores for all (or a subset) of alleles at the (Nj) gene-specific genetic loci may be combined to determine an overall probability $P_j$ of altering the gene product from gene $Q_j$. For example, the probability $P_j$ of altering the gene product from gene $Q_j$ associated with each individual parent (p) may be $(1-\Pi_{k=1}^{Nj}[1-\hat{s}_{j,k}^P])$, where $\hat{s}_{j,k}^P$ is the gene-(j) specific score assigned to the allele located at the kth genetic locus (k runs from a first (k=1) to a last (k=Nj) of the (Nj) gene-specific loci). Since $\hat{s}_{j,k}^P$ represents the probability of expression or expressivity associated with an allele at the kth locus, $(1-\hat{s}_{j,k}^P)$ may represent the probability of alteration of the gene product (e.g., loss of function of the gene product) associated with the allele at the kth locus, $\Pi_{k=1}^{Nj}[1-\hat{s}_{j,k}^P]$ may represent the combined probability that the gene product associated with alleles at all Nj gene-(Qj) loci is not altered, and $(1-\Pi_{k=1}^{Nj}[1-\hat{s}_{j,k}^P])$ may represent the combined probability of alteration of the gene product associated with alleles at all Nj gene-(Qj) loci. For a recessive phenotype, the probability $P_j$ of having the gene-(Qj) phenotype $Ph_j$ in a progeny of two potential parents (p1) and (p2) may be the product of the probabilities associated with each individual parent, e.g. $P_j^{p1,p2}=(1-\Pi_{k=1}^{Nj}[1-\hat{s}_{j,k}^{p1}])(1-\Pi_{k=1}^{Nj}[1-\hat{s}_{j,k}^{p2}])$. For a dominant phenotype, the probability $P_j$ of having the gene-(Qj) phenotype $Ph_j$ in a progeny of two potential parents (p1) and (p2) may be the sum of the probabilities associated with each individual parent, e.g., $p_j^{p1,p2}=(1-\Pi_{k=1}^{Nj}[1-\hat{s}_{j,k}^{p1}])+(1-\Pi_{k=1}^{Nj}[1-\hat{s}_{j,k}^{p2}])$. Other probabilities or derivations or modifications of the aforementioned probabilities may be used.

The probability of expression $P_j$ (e.g. generated by either the matching or scoring methods) may be used to determine a phenotype outcome for each living or virtual progeny. A continuous range of outcomes (e.g. such as a percentage) or a plurality of discrete outcomes (e.g., no expression, mild, moderate, severe or complete expression, or any other categories) may be used to define a degree or likelihood of phenotype expression. Discrete outcomes may be determined by comparing the probability $P_j$ (or a derivation thereof) to one or more threshold ranges each associated with a different outcome category and selecting the outcome category associated with the threshold range satisfied by the probability.

In embodiments in which scores define a degree of alteration of a gene product, the degree of alteration may be equated with the probability $P_j$ (or a derivation thereof). In embodiments in which scores define likelihoods of complete expression, a random number may be used to determine if the phenotype completely expresses or not, and if the phenotype is determined to completely express, the likelihood of complete expression may be equated with the probability $P_j$ (or a derivation thereof). The random number may be used to simulate the indeterminate nature of phenotype expression.

The genetic information for a living organism is unique. Accordingly, a single iteration of the scoring or matching process may be executed to generate a single probability of expression $P_j$ for the living organism. However, for a virtual organism, the genetic information is not known but predicted, and thus a plurality (e.g. thousands) of virtual progeny genome samplings $G_t$ may be generated in a virtual progeny genome $G^{VP}$. Accordingly, the aforementioned processes may be repeated for each of the plurality of virtual progeny genome samplings $G_i$ and the resulting probabilities and/or outcomes may be combined, for example, to produce an average, median or mode single outcome or a statistical distribution of outcomes.

The aforementioned processes may generate the probability $P_j$ of degree or likelihood of expression for a phenotype associated with a single gene $Q_j$. Such processes may be repeated for each of a plurality of genes (j=1, . . . , J).

The following discussion of diseases or mutations is provided as an example and these embodiments may relate to any phenotype. Embodiments of the invention may use genetic information, such as, established disease genotypes (e.g. for the matching method) and variant risk of impact on gene product (e.g. for the scoring method).

The established disease genotypes database may include information representing diploid genotypes found previously in individual persons together with empirically derived values for expressivity and penetrance. Resources for the derivation of this table include the genotype-phenotype correlations section of each disease record in Gene Reviews at the NCBI, the Allelic Variants section of the OMIM database, and other databases maintained by NCBI or other organizations. Genotypes may be single locus or multi-locus.

The variant risk of impact on gene product may include information representing known and/or postulated DNA variant alleles in each recessive gene together with computationally derived scores. The scores may describe the likely impact on the gene product of a gene copy containing the variant. Scores may range in value between, for example, zero and one (or indicating probabilities in a range from zero to one). Scores may be generated through the integration of data obtained from computational tools such as PolyPhen, which evaluates the likelihood that a specific amino acid substitution will damage protein function, and Provean, which implements a damage potential algorithm based on natural selection, for example, by detecting changes in amino acids and determining if such change is tolerated in other species. Provean and PolyPhen may be used to predict loss-of-function and gain-of-function mutations.

In one example, a score of 0.0 may indicate that an allele that has no impact on gene function and a score of 1.0 may indicate that an allele is likely to eliminate 100% of gene function with 100% probability, and scores between 0.0 and 1.0 represent corresponding intermediate degrees or likelihoods of gene damage, although any other scores may be used. The score may be interpreted as a likelihood of the loss of function of the gene product (e.g., protein inactivation or as a relative reduction in protein activity).

Virtual gametes from hypothetical or maternal (M) and paternal (P) potential parents may be constructed, e.g. as described herein and/or in US Patent Application Publication No. 2011/0124515, which is hereby incorporated by reference in its entirety. Two virtual gametes are combined (M×P) to produce a discrete virtual progeny genome (G). Virtual progeny genome (G) may be represented, for example, as an (N×2) dimensional data structure such as a table, matrix, or sequence, defining alleles $h_i^m$ and $h_i^p$ at the N genome loci of each of the maternal ($H^m$) and paternal ($H^p$) haplopaths, for example, as follow.

$$G^{M \times P} = \{[h_i^m, h_i^p]; i=1, \ldots, N\}$$

In accordance with the matching method, the two alleles at each individual locus of the virtual progeny genome G may be combined into a third set of genotypes. Embodiments of the invention may interrogate or search for this set of genotypes in the established disease genotype database. If a match is detected, a random number may be used to determine whether the specific virtual progeny under investigation is affected. If affected, the severity of the disease may be defined as the expressivity value (or a function thereof).

In accordance with the scoring method, alleles $h_i^m$ and $h_i^p$ in each haplopath ($H^m$) and ($H^p$) of the virtual progeny genome G may be mapped by a one-to-one mapping to corresponding scores $s_i^m$ and $s_i^p$, for example, as follows.

$$[h_i^m, h_i^p] \to [S_i^m, S_i^p]$$

In various embodiments, every allele in G may be assigned a score, or only a subset of alleles may be assigned scores, e.g., only alleles at the (Nj) gene-specific loci. Normal (non-mutant) alleles may have scores of zero, which may (or may not) be recorded along with non-zero scores for other alleles.

The following describes scoring method steps executed for a maternal haplopath. A parallel process may be executed for the paternal haplopath.

Haplopaths may be divided into subsets of SNPs or other alleles associated with each gene or complementation group Q under investigation. Genes Qj may be indexed on j. Gene-specific loci associated with a disease gene may be indexed on k. A gene-specific score may be distinguished from a general penetrance or expressivity score s by the variable symbol $\bar{s}$. The gene index j may be indicated as a first subscript value and the second subscript may indicate the gene-specific locus k. Every gene Qj may have a defined rule set of the following form (indicated for the maternal haplopath).

$$Q_j^m : \{s_i^m \to \bar{s}_{j,k}^m; k=1, \ldots, N_j\}$$

For example, disease gene Q3 may encompass alleles indexed at genetic loci i=5, i=9, i=25, and i=30 on a master virtual progeny genome. Scores for alleles indexed at the gene Q3-specific loci i may be mapped to sequential k-values, e.g. beginning with i=1, according to a Q3 mapping rule associated with gene Qj. The mapping rule, which is a re-indexing, may be represented as follows:

$$Q_3^m : \{s_5^m \to \bar{s}_{3,1}^m; s_9^m \to \bar{s}_{3,2}^m; s_{25}^m \to \bar{s}_{3,3}^m; s_{30}^m \to \bar{s}_{3,4}^m\}$$

Alteration of gene function (e.g., protein damage) may be caused by any of multiple variants within each gene Qj. The probability of alteration of the gene product (e.g., damage or inactivity of the protein product) may be computed individually for each copy of gene Qj, for example, as follows.

$$P_j^m = \left(1 - \prod_{k=1}^{N_j} [1 - \bar{s}_{j,k}^m]\right)$$

For example, when the gene product is a protein, the probability of a functional protein is the joint probability that none of the gene's allele variants cause inactivation. In other words, the probability of a functional protein is the product of the terms (1-damage score) for each variant as shown in the right-most term of the equation above. The probability of damage is calculated by subtracting the product term from 1.

For a recessive disease or phenotype, based on the penetrance or expressivity model, the likelihood of disease in a virtual progeny may be the joint probability that both parents' gene copies are defective. This genome probability is the product of the maternal and paternal probabilities, for example:

$$\left(1 - \prod_{k=1}^{N_j} [1 - \hat{s}_{j,k}^m]\right)\left(1 - \prod_{k=1}^{N_j} [1 - \hat{s}_{j,k}^p]\right)$$

For a dominant incompletely penetrant disease or phenotype, the likelihood of disease in a virtual progeny may be the probability that either parent's gene copy is defective. This genome probability is the sum of the maternal and paternal probabilities, for example, since the inactivity of either one is sufficient to cause disease in the progeny.

$$\left(1 - \prod_{k=1}^{N_j} [1 - \hat{s}_{j,k}^m]\right)\left(1 - \prod_{k=1}^{N_j} [1 - \hat{s}_{j,k}^p]\right)$$

In some embodiments, scores may define likelihoods of complete protein inactivation. In such cases, a random number generator may be used to determine whether or not the associated phenotype $Ph_j$ is expressed, for example, such that the particular gene copy produces a dysfunctional protein or not. For phenotype $Ph_j$, the probability $P_j$ may define a penetrance or expressivity factor or likelihoods of expression associated with each copy of each gene Qj.

In some embodiments, scores may define a relative reduction in protein activity or degree of expressivity rather than a probability of complete inactivation. In such embodiments, the probability $P_j$ may be interpreted as an indication of functional protein level and one or more thresholds defining different severities of disease may be applied to the probability to determine the severity of expression (e.g., no expression, mild, moderate, severe or complete expression).

Figure 3:
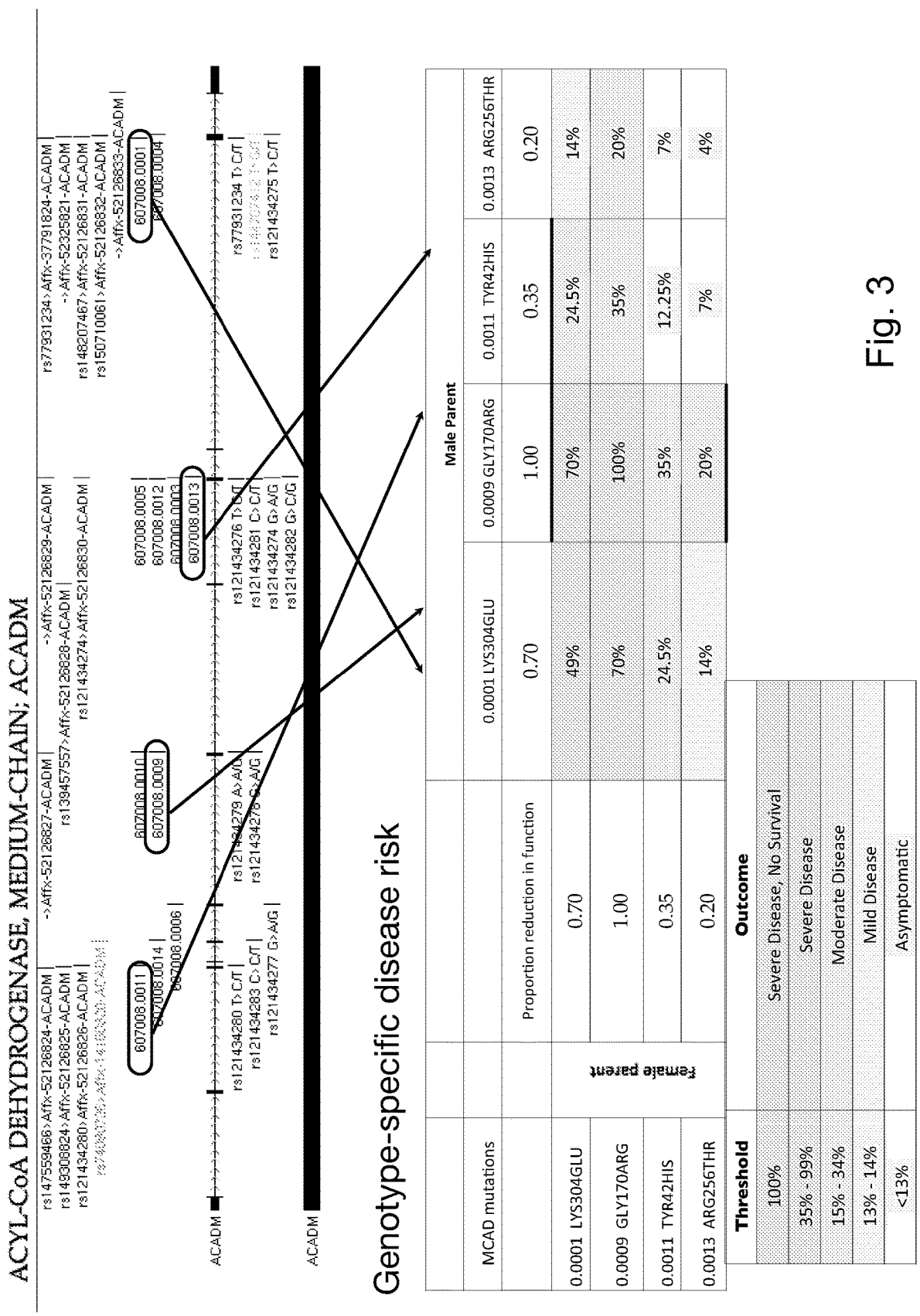
FIG. 3 is a diagram of results of testing for expression of the MCAD deficiency due to any of four known mutations of the ACADM gene in accordance with embodiments of the invention.

Reference is made to FIG. 3, which is a diagram of results of testing for expression of the MCAD deficiency due to any of four known mutations of the ACADM gene in accordance with embodiments of the invention.

The following table lists four mutations of the ACADM gene responsible for the recessive disease MCAD deficiency. Each mutation is identified by a decimal number assignment from the OMIM database at NCBI and a identification code including a three letter code identifying the amino acid in the normal protein, followed by a number indicating the position of the amino acid in the protein, followed by a three letter code identifying a replacement amino acid caused by the mutation. The second column provides a probability $P_j^p$ of protein damage associated with each of the second listed amino acids for each parent. In this example, the first amino acid of each row may be assumed to be "normal" and has a damage score of zero (not shown), although in some cases, a "normal" or non-variant allele may have a non-zero score.

| 0.0001 | LYS304GLU | 0.70 |
| 0.0009 | GLY170ARG | 1.00 |
| 0.0011 | TYR42HIS | 0.35 |
| 0.0013 | ARG256THR | 0.20 |

Since MCAD deficiency is a recessive disease, the probability $P_j^{p1,p2}$ of protein damage for each combination of mutations in the progeny of the two parents (p1) and (p2) is the product of the probabilities associated with each individual parent $P_j^p$. For example, each of the 16 row-column entries defines a total probability for a different one of the 16 possible mutant combinations.

In the example of FIG. 3, the probabilities of protein damage may be equated with the severity of protein dysfunction. The probabilities may be compared to one or more threshold ranges each associated with a different outcome of the severity of protein dysfunction. Threshold ranges of, for example, 0%-13%, 13%-14.$\overline{9}$%, 15%-34.$\overline{9}$%, and 35%-99.$\overline{9}$% are associated with outcomes, such as, asymptomatic, mild disease, moderate disease, severe disease and severe disease with no survival, respectively.

The probabilities for multiple mutation pairs may be combined into a single probability and/or outcome for each real genome or set of virtual progeny genomes generated for a single pairing of potential parents (e.g. referred to as a "virtual progeny"). For a virtual progeny having a plurality of genome samplings $G_i$, the resulting probabilities and/or outcomes may be combined, for example, to produce an average, median or mode single outcome or a statistical distribution of outcomes.

Figure 5:
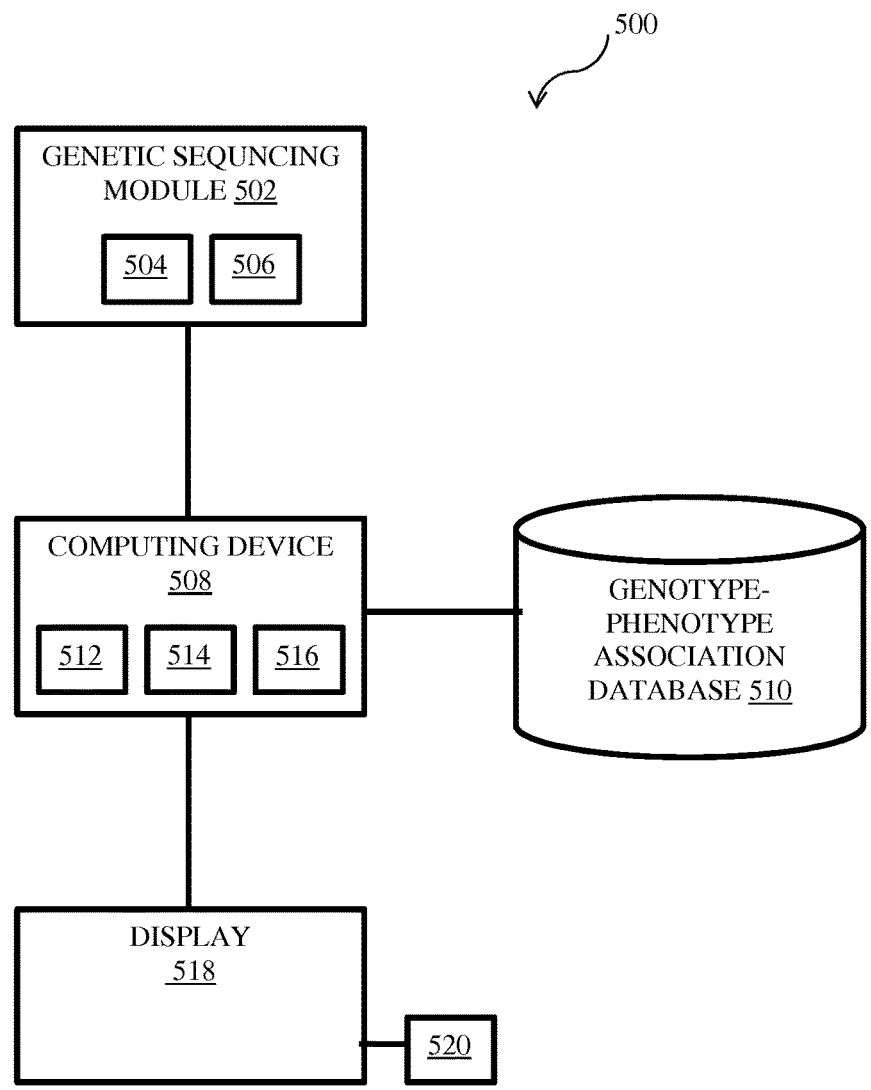
FIG. 5 is a schematic illustration of a system according to an embodiment of the invention.

FIG. 5 is a schematic illustration of a system 500 according to an embodiment of the invention. Methods disclosed herein may be performed using the system of FIG. 5.

System 500 may include a genetic sequencing module 502 that accepts genetic material or DNA samples from each of a plurality of living donors and generates a genome or genome profile for each donor. Genetic sequencing module 502 may include a processor 504 for generating each donor's genome profile and a memory 506 for storing each donor's genome profile.

Computing device 508 may include, for example, any suitable processing system, computing system, computing device, processing device, computer, processor, or the like, and may be implemented using any suitable combination of hardware and/or software. Computing device 508 may include for example one or more processor(s) 512, memory 514 and software 516. Data generated by genetic sequencing module 502, such as each donor's genome profile, may be transferred, for example, to computing device 508. The data may be stored in the memory 514 as for example digital information and transferred to computing device 508 by uploading, copying or transmitting the digital information. Processor 504 may communicate with computing device 508 via wired or wireless command and execution signals.

Computing device 508 may use each donor's genome information to generate a virtual gamete or haplopath for the donor. Computing device 508 may combine the virtual gametes from pairs of donors to generate a virtual progeny genome sampling to simulate the mating of one donor with another individual donor or with each of a pool of potential donors. Computing device 508 may repeat the process to generate a virtual progeny genome for each pair of potential parents. Computing device 508 may analyze the virtual progeny genome of the potential parents to predict whether a virtual progeny potentially to be conceived will have phenotypes $Ph_j$ associated with a single gene $Q_j$ by those potential parents as described herein.

In some embodiments using a matching method, computing device 508 may compare genotypes in the virtual progeny genome to genotypes in a genotype-phenotype association database 510 to detect any genotype-phenotype matches. Genotype-phenotype association database 510 may connect to computing device 508 via a wired or wireless connection.

In some embodiments using a scoring method, computing device 508 may compute scores associated with genotypes in the virtual progeny genome or retrieve scores from an external score database.

Memory 506 and 514 and database 510 may include cache memory, long term memory such as a hard drive, and/or external memory, for example, including random access memory (RAM), read only memory (ROM), dynamic RAM (DRAM), synchronous DRAM (SD-RAM), flash memory, volatile memory, non-volatile memory, cache memory, buffer, short term memory unit, long term memory unit, or other suitable memory units or storage units. Memory 506 and 514 and database 510 may store instructions (e.g., software 516) and data to execute embodiments of the aforementioned methods, steps and functionality (e.g., in long term memory, such as a hard drive).

Computing device 508 may include a computing module having machine-executable instructions. The instructions may include, for example, a data processing mechanism (including, for example, embodiments of methods described herein) and a modeling mechanism. These instructions may be used to cause processor 512 using associated software 516 modules programmed with the instructions to perform the operations described. Alternatively, the operations may be performed by specific hardware that may contain hard-wired logic for performing the operations, or by any combination of programmed computer components and custom hardware components.

Embodiments of the invention may include an article such as a computer or processor readable medium, or a computer or processor storage medium, such as for example a memory, a disk drive, or a USB flash memory, encoding, including or storing instructions, e.g., computer-executable instructions, which when executed by a processor or controller, carry out methods disclosed herein.

Processor 512 may perform various methods described herein. For example, processor 512 may execute methods 600 and 700 of FIGS. 6 and 7.

Display 518 may display results and/or intermediate data such as outcomes, probabilities, virtual progeny phenomes, for example, as shown in the diagram of FIG. 3. Display 518 may include a monitor or screen, such as an organic light emitting diode (LED) screen, liquid crystal display (LCD) screen, thin film transistor display, or the like. In one embodiment, the user may interact with display 580 using input device(s) 520.

Input device(s) 520 may include a keyboard, pointing device (e.g., mouse, trackball, pen,), a touch screen or cursor direction keys, communicating information and command selections to processor 514. Input device 520 may communicate user direction information and command selections to the processor 514. For example, a user may use input device 520 to select donors for testing, define genes and/or phenotypes to be under investigation, set thresholds or phenotype categories, set margins of error or certainty of calculations, etc.

Processor 504 and 514 may include, for example, one or more processors, controllers, central processing units ("CPUs"), or graphical processing units ("GPUs"). Software 516 may be stored, for example, in memory 514.

Figure 6:
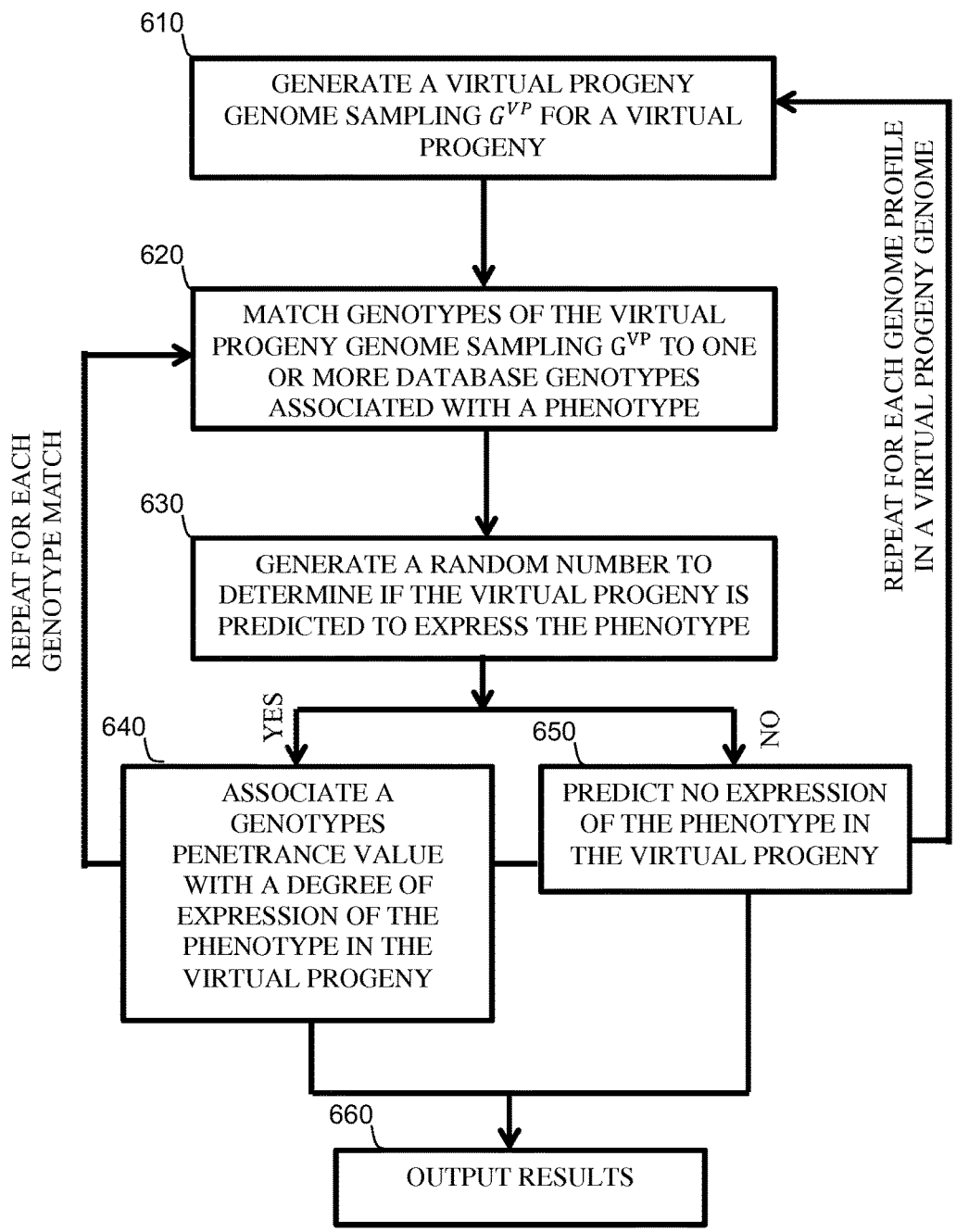
FIG. 6 is a flowchart of a matching method for predicting the expression of phenotypes in progeny according to embodiments of the invention.

Reference is made to FIG. 6, which is a flowchart of a matching method 600 for predicting the expression of phenotypes in progeny according to embodiments of the invention. Method 600 may be implemented by a computer processor (e.g. processor 514 of FIG. 5) executing program instructions (e.g. in software 516 of FIG. 5).

In operation 610, a processor (e.g. processor 514 of FIG. 5) may be adapted to generate a virtual progeny genome sampling $G=\{[h_i^{p1}, h_i^{p2}]; i=1, \ldots, N\}$ for a virtual progeny. The virtual progeny genome sampling G may include, at each of a plurality of genetic loci $i=1, \ldots, N$, one allele $h_i^{p1}$ from a first genome profile of a first potential parent (p1) and one allele $h_i^{p2}$ from a second genome profile of a second potential parent (p2). In one embodiment, the set of alleles $\{h_i^p, i=1, \ldots, N\}$ for each potential parent $p=(p1, p2)$ is a haplopath $H^p$ generated by selecting one of the two alleles $h_i^p \in (1,2)$ at each genetic locus along a path of the genome profile of the potential parent. The two haplopaths $H^{p1}$ and $H^{p2}$ may form two virtual gametes from respective parents (p1) and (p2), which may be combined to generate the virtual progeny genome sampling G.

In operation 620, the processor may be adapted to compare genotypes for a gene Qj of the virtual progeny genome sampling G to one or more databases of genotype-phenotype associations (e.g. genotype-phenotype association database 510 of FIG. 5) to determine a phenotype associated with database genotypes matching genotypes of said virtual progeny genome sampling G. Each genotype-phenotype may be associated with a penetrance or expressivity value indicating the empirically observed likelihood that a phenotype will be expressed in a progeny having the associated genotype.

In operation 630, the processor may be adapted to generate a random number to determine if the virtual progeny is predicted to express the phenotype. For example, the random number may oscillate randomly between 0 (no expression) and 1 (expression), or on a scale e.g. 1-10 and may be compared to a threshold e.g. of 5, for an equal probability of expression and non-expression. In some examples, a phenotype may be biased to express or non-express with a non-equal probability, in which case the random number may be weighted by a bias factor or the threshold may be shifted to bias the outcome to either express or non-express according to a predefined bias ratio. In the absence of such randomization, genotypes and phenotypes are exactly correlated, which does not generally occur in nature and thus, provides less accurate results than embodiments of the invention using the random number to determine expression. If the virtual progeny is predicted to express the phenotype, a process or processor may proceed to operation 640. Otherwise, a process or processor may proceed to operation 650.

In operation 640, the processor may be adapted to predict positive expression of the phenotype in the virtual progeny with a degree of expression equal the penetrance or expressivity value (or a derivation thereof). If the phenotype is a disease, the degree of expression may define the severity of the disease (e.g. as shown in FIG. 3).

In operation 650, the processor may be adapted to predict a negative expression of the phenotype in the virtual progeny.

After operation 640 or 650, a process or processor may repeat operations 610-650 for a plurality of different virtual progeny genome samplings $G^{VP}=\{G_1, G_2, \ldots, G_M\}$, where each sampling may differ from each other sampling by at least one or more alleles.

After operation 640 or 650, a process or processor may repeat operations 620-650 to determine phenotypic expression for another genotype match for another gene $Q_{j+1}$ in the virtual progeny genome profile.

In operation 660, the processor may be adapted to output or display (e.g. on display 518 of FIG. 5) the probability of expression of the phenotype $Ph_j$ or a derivation thereof for one or more genes $Q_j$.

Other operations or orders of operations may be used. In various embodiments, operations 610-650 may be repeated before, after, or in parallel (simultaneously to) repeating operations 620-650. In one example, a single, multiple or multi-core processor may execute operations 610-650 for a plurality of the virtual progeny genome sampling $G_i$ in parallel for predicting the expression of a phenotype associated with a single gene $Q_j$, and in each consecutive series of operations the processor may predict for the samplings $G_i$ the expression of a phenotype associated with a sequential gene $Q_{j+1}$, for example, until matching genotypes for all $j=1, \ldots, J$ genes are analyzed.

Figure 7:
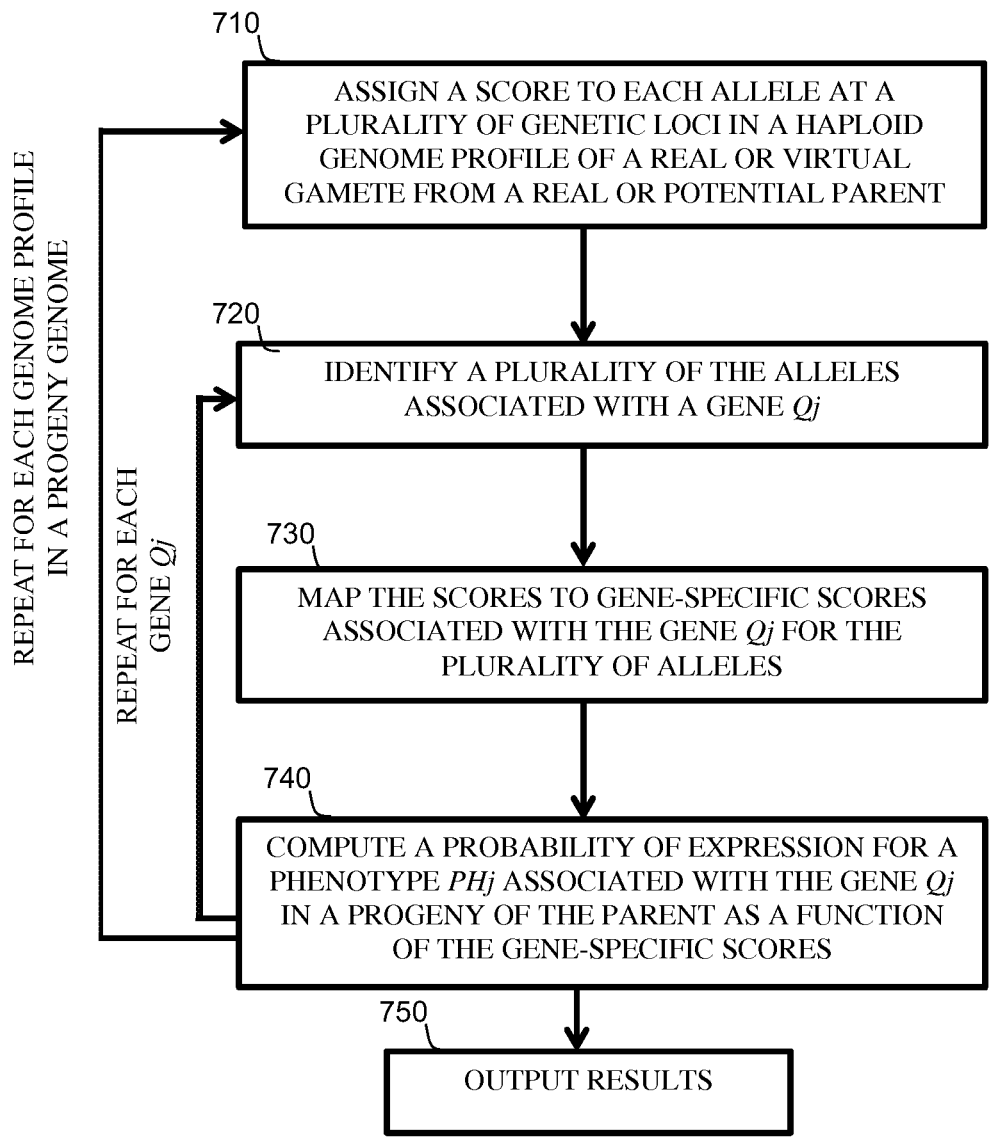
FIG. 7 is a flowchart of a scoring method for predicting the expression of phenotypes in progeny according to embodiments of the invention.

FIG. 7 is a flowchart of a scoring method for predicting whether progeny will one or more phenotypes $Ph_j$ each associated with a single gene $Q_j$ according to embodiments of the invention. Method 700 may be implemented by a computer processor (e.g. processor 514 of FIG. 5) executing program instructions (e.g. in software 516 of FIG. 5).

In operation 710, a processor (e.g. processor 514 of FIG. 5) may be adapted to generate a haplopath $H^p = \{h_1^p, h_2^p, \ldots, h_N^p\}$ including a single allele $h_i^p \in (1,2)$ at each of a plurality of loci ($i=1, \ldots, N$) from a genome profile of a potential parent (p).

In operation 720, the processor may be adapted to assign a score $s_i^p$ to each allele $h_i^p$ at a plurality of genetic loci (i) in a haploid genome profile $H^p$ of a parent (p). Scores $s_i^p$ may indicate a probability that the allele $h_i^p$ results in expression of a variant trait or genotype in progeny, a probability that the variant allele $h_i^p$ indicating an amino acid substitution at the locus (i) will damage protein function, and/or a probability that the variant allele $h_i^p$ indicating a change in one or more amino acids will occur randomly based on natural selection.

In operation 720, the processor may be adapted to identify a plurality ($N_j$) of the alleles $h_k^p$ ($k=1, \ldots, N_j$) associated with the gene $Q_j$.

In operation 730, the processor may be adapted to map the scores $s_i^p$ to gene-specific scores $\hat{s}_{j,k}^p$ associated with gene $Q_j$ for the plurality of ($N_j$) alleles $h_k^p$.

In operation 740, the processor may be adapted to compute a probability of having the phenotype $Ph_j$ associated with gene $Q_j$ in a progeny of the parent (p) to be a function of the gene-specific scores $\hat{s}_{j,k}^p$. In one embodiment, the scores or probability may indicate a likelihood of expression of the phenotype $Ph_j$ in the virtual progeny, a random number generator (e.g. executed by processor 514) may generate a random number to predict if the phenotype $Ph_j$ will express in the progeny (e.g. as described in reference to operations 630-650 of FIG. 6). In one embodiment, the scores or probability may indicate a degree of expressivity of the phenotype $Ph_j$ in the progeny. The probability may be compared to one or more thresholds to determine a category of severity of the expression of the phenotype $Ph_j$.

Operation 710-740 may be repeated for a plurality of different virtual progeny genome samplings $G^{VP} = \{G_1, G_2, \ldots, G_M\}$ and/or operations 720-740 may be repeated for a plurality of different genes $Qj, j=1, \ldots, J$, for example, as described in reference to FIG. 6.

In operation 750, the processor may be adapted to output or display (e.g. on display 518 of FIG. 5) the probability of expression of the phenotype $Ph_j$ or a derivation thereof for one or more genes $Q_j$.

Other operations or orders of operations may be used.

The aforementioned block diagrams illustrate the architecture, functionality, and operation of possible implementations of systems and methods according to various embodiments of the present invention. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

Nonlimiting examples of phenotypes that may be assessed using the methods described herein include or relate to ability to roll the tongue, ability to taste PTC, acute inflammation, adaptive immunity, addiction(s), adipose tissue, adrenal gland, age, aggression, amino acid level, amyloidosis, anogenital distance, antigen presenting cells, auditory system, autonomic nervous system, avoidance learning, axial defects or lack thereof, B cell deficiency, B cells, B lymphocytes (e.g., antigen presentation), basophils, bladder size/shape, blinking, blood chemistry, blood circulation, blood glucose level, blood physiology, blood pressure, body mass index, body weight, bone density, bone marrow formation/structure, bone strength, bone/skeletal physiology, breast size/shape, bursae, cancellous bone, cardiac arrest, cardiac muscle contractility, cardiac output, cardiac stroke volume, cardiomyopathy, cardiovascular system/disease, carpal bone, catalepsy, cell abnormalities, cell death, cell differentiation, cell morphology, cell number, cell-mediated immunity, central nervous system, central nervous system physiology, chemotactic factors, chondrodystrophy, chromosomal instability, chronic inflammation, circadian rhythm, circulatory system, cleft chin, clonal anergy, clonal deletion, T and B cell deficiencies, conditioned emotional response, congenital skeletal deformities, contextual conditioning, cortical bone thickness, craniofacial bones, craniofacial defects, crypts of Lieberkuhn, cued conditioning, cytokines, delayed bone ossification, dendritic cells (e.g., antigen presentation), Di George syndrome, digestive function, digestive system, digit dysmorphology, dimples, discrimination learning, drinking behavior, drug abuse, drug response, ear size/shape including ear lobe attachment, eating behavior, ejaculation function, embryogenesis, embryonic death, embryonic growth/weight/body size, emotional affect, enzyme/coenzyme level, eosinophils, epilepsy, epiphysis, esophagus, excretion physiology, extremities, eye blink conditioning, eye color/shape, eye physiology, eyebrows shape, eyelash length, face shape, facial cleft, femur, fertility/fecundity, fibula, finger length/shape, fluid regulation, fontanels, foregut, fragile skeleton, freckles, gall bladder, gametogenesis, gastrointestinal hemorrhage, germ cells (e.g., morphology, depletion), gland dysmorphology, gland function, glucagon level, glucose homeostasis, glucose tolerance, glycogen catabolism, granulocytes, granulocytes (e.g., bactericidal activity, chemotaxis), grip strength, grooming behavior, hair color, hair follicle structure/orientation, hair growth, hair on mid joints, hair texture, handedness, harderian glands, head, hearing function, heart, heart rate, heartbeat (e.g., rate, irregularity), height, hemarthrosis, hemolymphoid system, hepatic system, hitchhiker's thumb, homeostasis, humerus, humoral immune response, hypoplastic axial skeleton, hypothalamus, immune cell, immune system (e.g., hypersensitivity), immune system response/function, immune tolerance, immunodeficiency, inability to urinate, increased sensitivity to gamma-irradiation, inflammatory mediators, inflammatory response, innate immunity, inner ear, innervation, insulin level, insulin resistance, intestinal bleeding, intestine, ion homeostasis, jaw, kidney hemorrhage, kidney stones, kidney/renal system, kyphoscoliosis, kyphosis, lacrimal glands, larynx, learning/memory, leukocyte, ligaments, limb dysmorphology, limb grasping, lipid chemistry, lipid homeostasis, lips size/shape, liver (e.g., development/function), liver/hepatic system, locomotor activity, lordosis, lung, lung development, lymph organ development, macrophages (e.g., antigen presentation), mammary glands, maternal/paternal behavior, mating patterns, meiosis, mental acuity, mental stability, mental state, metabolism of xenobiotics, metaphysis, middle ear, middle ear bone, morbidity and mortality, motor coordination/balance, motor learning, mouth, movement, muscle, muscle contractility, muscle degeneration, muscle development, muscle physiology, muscle regeneration, muscle spasms, muscle twitching, musculature, myelination, myogenesis, nervous system, neurocranium, neuroendocrine glands, neutrophils, NK cells, nociception, nose, nutrients/absorption, object recognition memory, ocular reflex, odor preference, olfactory system, oogenesis, operant or "target response", orbit, osteogenesis, osteogenesis/developmental, osteomyelitis, osteoporosis, outer ear, oxygen consumption, palate, pancreas, paralysis, parathyroid glands, pelvis girdle, penile erection function, perinatal death, peripheral nervous system, phalanxes, pharynx, photosensitivity, piloerection, pinna reflex, pituitary gland, PNS glia, postnatal death, postnatal growth/weight/body size, posture, premature death, preneoplasia, propensity to cross the right arm over the left of vice versa, propensity to cross the right thumb over the left thumb when clasping hands or vise versa, pulmonary circulation, pupillary reflex, radius, reflexes, reproductive condition, reproductive system, resistance to fatty liver development, resistance to hyperlipidemia, respiration (e.g., rate, shallowness), respiratory distress or failure, respiratory mucosa, respiratory muscle, respiratory system, response to infection, response to injury, response to new environment (transfer arousal), ribs, salivary glands, scoliosis, sebaceous glands, secondary bone resorption, seizures, self tolerance, senility, sensory capabilities, sensory system physiology/response, sex, sex glands, shoulder, skin, skin color, skin texture/condition, skull, skull abnormalities, sleep pattern, social intelligence, somatic nervous system, spatial learning, sperm count, sperm motility, spermatogenesis, startle reflex, sternum defect, stomach, suture closure, sweat glands, T cell deficiency, T cells (e.g., count), tarsus, taste response, teeth, temperature regulation, temporal memory, tendons, thyroid glands, tibia, touch/nociception, trachea, tremors, trunk curl, tumor incidence, tumorigenesis, ulna, urinary system, urination pattern, urine chemistry, urogenital condition, urogenital system, vasculature, vasoactive mediators, vertebrae, vesicoureteral reflux, vibrissae, vibrissae reflex, viscerocranium, visual system, weakness, widows peak or lack thereof, etc.

Other nonlimiting phenotypes include cognitive ability (Ruano et al., Am. J. Hum. Genet. 86:113 (2010)); Familial Osteochondritis Dissecans (Stattin et al., Am. J. Hum. Genet. 86:126 (2010)); hearing impairment (Schraders et al., Am. J. Hum. Genet. 86:138 (2010)); mental retardation associated with autism, epilepsy, or macrocephaly (Giannandrea et al., Am. J. Hum. Genet. 86:185 (2010)); muscular dystrophies (Bolduc et al., Am. J. Hum. Genet. 86:213 (2010)); Diamond-Blackfan anemia (Doherty et al., Am. J. Hum. Genet. 86:222 (2010)); osteoporotic fractures (Kung et al., Am. J. Hum. Genet. 86:229 (2010)); familial exudative vitreoretinopathy (Poulter et al., Am. J. Hum. Genet. 86:248 (2010)); skeletal dysplasia, eye, and cardiac abnormalities (Iqbal et al., Am. J. Hum. Genet. 86:254 (2010)); Warsaw breakage syndrome (van der Lilij et al., Am. J. Hum. Genet. 86:262 (2010)); arterial calcification of infancy (Lorenz-Depiereux et al., Am. J. Hum. Genet. 86:267 (2010)); hypophosphatemic rickets (Lorenz-Depiereux et al., Am. J. Hum. Genet. 86:267 (2010); Levy-Litan et al., Am. J. Hum. Genet. 86:273 (2010)); rhabdoid tumor predisposition syndrome (Schneppenheim et al., Am. J. Hum. Genet. 86:279 (2010)); and multiple sclerosis (Jakkula et al., Am. J. Hum. Genet. 86:285 (2010)).

Yet other nonlimiting phenotypes include 21-Hydroxylase Deficiency, ABCC8-Related Hyperinsulinism, ARSACS, Achondroplasia, Achromatopsia, Adenosine Monophosphate Deaminase 1, Agenesis of Corpus Callosum with Neuronopathy, Alkaptonuria, Alpha-1-Antitrypsin Deficiency, Alpha-Mannosidosis, Alpha-Sarcoglycanopathy, Alpha-Thalassemia, Alzheimers, Angiotensin II Receptor, Type I, Apolipoprotein E Genotyping, Argininosuccinicaciduria, Aspartylglycosaminuria, Ataxia with Vitamin E Deficiency, Ataxia-Telangiectasia, Autoimmune Polyendocrinopathy Syndrome Type 1, BRCA1 Hereditary Breast/Ovarian Cancer, BRCA2 Hereditary Breast/Ovarian Cancer, Bardet-Biedl Syndrome, Best Vitelliform Macular Dystrophy, Beta-Sarcoglycanopathy, Beta-Thalassemia, Biotinidase Deficiency, Blau Syndrome, Bloom Syndrome, CFTR-Related Disorders, CLN3-Related Neuronal Ceroid-Lipofuscinosis, CLN5-Related Neuronal Ceroid-Lipofuscinosis, CLN8-Related Neuronal Ceroid-Lipofuscinosis, Canavan Disease, Carnitine Palmitoyltransferase IA Deficiency, Carnitine Palmitoyltransferase II Deficiency, Cartilage-Hair Hypoplasia, Cerebral Cavernous Malformation, Choroideremia, Cohen Syndrome, Congenital Cataracts, Facial Dysmorphism, and Neuropathy, Congenital Disorder of Glycosylationla, Congenital Disorder of Glycosylation Ib, Congenital Finnish Nephrosis, Crohn Disease, Cystinosis, DFNA 9 (COCH), Diabetes and Hearing Loss, Early-Onset Primary Dystonia (DYT1), Epidermolysis Bullosa Junctional, Herlitz-Pearson Type, FANCC-Related Fanconi Anemia, FGFR1-Related Craniosynostosis, FGFR2-Related Craniosynostosis, FGFR3-Related Craniosynostosis, Factor V Leiden Thrombophilia, Factor V R2 Mutation Thrombophilia, Factor XI Deficiency, Factor XIII Deficiency, Familial Adenomatous Polyposis, Familial Dysautonomia, Familial Hypercholesterolemia Type B, Familial Mediterranean Fever, Free Sialic Acid Storage Disorders, Frontotemporal Dementia with Parkinsonism-17, Fumarase deficiency, GJB2-Related DFNA 3 Nonsyndromic Hearing Loss and Deafness, GJB2-Related DFNB 1 Nonsyndromic Hearing Loss and Deafness, GNE-Related Myopathies, Galactosemia, Gaucher Disease, Glucose-6-Phosphate Dehydrogenase Deficiency, Glutaricacidemia Type 1, Glycogen Storage Disease Type 1a, Glycogen Storage Disease Type Ib, Glycogen Storage Disease Type II, Glycogen Storage Disease Type III, Glycogen Storage Disease Type V, Gracile Syndrome, FIFE-Associated Hereditary Hemochromatosis, Halder AIMs, Hemoglobin S Beta-Thalassemia, Hereditary Fructose Intolerance, Hereditary Pancreatitis, Hereditary Thymine-Uraciluria, Hexosaminidase A Deficiency, Hidrotic Ectodermal Dysplasia 2, Homocystinuria Caused by Cystathionine Beta-Synthase Deficiency, Hyperkalemic Periodic Paralysis Type 1, Hyperornithinemia-Hyperammonemia-Homocitrullinuria Syndrome, Hyperoxaluria, Primary, Type 1, Hyperoxaluria, Primary, Type 2, Hypochondroplasia, Hypokalemic Periodic Paralysis Type 1, Hypokalemic Periodic Paralysis Type 2, Hypophosphatasia, Infantile Myopathy and Lactic Acidosis (Fatal and Non-Fatal Forms), Isovaleric Acidemias, Krabbe Disease, LGMD2I, Leber Hereditary Optic Neuropathy, Leigh Syndrome, French-Canadian Type, Long Chain 3-Hydroxyacyl-CoA Dehydrogenase Deficiency, MELAS, MERRF, MTHFR Deficiency, MTHFR Thermolabile Variant, MTRNR1-Related Hearing Loss and Deafness, MTTS1-Related Hearing Loss and Deafness, MYH-Associated Polyposis, Maple Syrup Urine Disease Type 1A, Maple Syrup Urine Disease Type 1B, McCune-Albright Syndrome, Medium Chain Acyl-Coenzyme A Dehydrogenase Deficiency, Megalencephalic Leukoencephalopathy with Subcortical Cysts, Metachromatic Leukodystrophy, Mitochondrial Cardiomyopathy, Mitochondrial DNA-Associated Leigh Syndrome and NARP, Mucolipidosis IV, Mucopolysaccharidosis Type I, Mucopolysaccharidosis Type IIIA, Mucopolysaccharidosis Type VII, Multiple Endocrine Neoplasia Type 2, Muscle-Eye-Brain Disease, Nemaline Myopathy, Neurological phenotype, Niemann-Pick Disease Due to Sphingomyelinase Deficiency, Niemann-Pick Disease Type C1, Nijmegen Breakage Syndrome, PPT1-Related Neuronal Ceroid-Lipofuscinosis, PROP1-related pituitary hormome deficiency, Pallister-Hall Syndrome, Paramyotonia Congenita, Pendred Syndrome, Peroxisomal Bifunctional Enzyme Deficiency, Pervasive Developmental Disorders, Phenylalanine Hydroxylase Deficiency, Plasminogen Activator Inhibitor I, Polycystic Kidney Disease, Autosomal Recessive, Prothrombin G20210A Thrombophilia, Pseudovitamin D Deficiency Rickets, Pycnodysostosis, Retinitis Pigmentosa, Autosomal Recessive, Bothnia Type, Rett Syndrome, Rhizomelic Chondrodysplasia Punctata Type 1, Short Chain Acyl-CoA Dehydrogenase Deficiency, Shwachman-Diamond Syndrome, Sjogren-Larsson Syndrome, Smith-Lemli-Opitz Syndrome, Spastic Paraplegia 13, Sulfate Transporter-Related Osteochondrodysplasia, TFR2-Related Hereditary Hemochromatosis, TPP1-Related Neuronal Ceroid-Lipofuscinosis, Thanatophoric Dysplasia, Transthyretin Amyloidosis, Trifunctional Protein Deficiency, Tyrosine Hydroxylase-Deficient DRD, Tyrosinemia Type I, Wilson Disease, X-Linked Juvenile Retinoschisis, and Zellweger Syndrome Spectrum.

Reference is made to FIG. 8, which lists genes and their associated diseases, which may be used for computer-generated diagnosis of the disease(s) in virtual progeny or the future emergence of the disease(s) in a living organism, according to embodiments of the invention. The gene-disease associations may be stored in one or more databases (e.g. database 510 of FIG. 5) for comparison with the virtual progeny or living organism genotypes for those genes.

The methods of assessing the probability that progeny will express certain phenotypes, as described herein, may be implemented into systems, programs, and/or services, which may be authorized by, referred by, and/or performed by, e.g., agencies, public or private companies, genetic counseling centers, dating or match-making services, sperm banks, egg providers, reproductive service providers, fertility clinics, or specialty laboratories.

Virtual Progeny Assessment and Genetic Counseling Referral System

In one example, the methods described herein are integrated into a testing service that may provide information to a couple on the probability that the couple's offspring will express one or more phenotypes described herein, such as risk of a disease. In addition to the results of the Virtual Progeny assessment, referrals to genetic counselors and/or other relevant medical professionals may be provided in order to provide for follow up testing and consultation.

In certain embodiments, a Virtual Progeny assessment begins with a customer order, and the customer may pay a service provider a fee in exchange for the assessment. A customer may be two potential parents, e.g., partners. Alternatively, a customer may be a physician, a genetic counselor, a medical center, an insurance company, a website, a dating service, a matchmaking service, a pharmaceutical company, or a laboratory testing service provider, who places an order on behalf of two potential parents. For example, a customer may be two prospective parents who seek to learn whether their offspring will be at risk for developing disease. After a customer places an order, DNA collection kits may be sent to the prospective parents, who may deposit a biological sample described herein into the collection kits. The collection kits may then be returned to the company for sending to a specialty lab or may be returned directly to the specialty lab for performing the assessment. A specialty lab, either internal within the company, contracted to work with the company, or external from the company, may isolate the potential parents' DNA from the provided samples for genome scanning from which Virtual Progeny may be generated, as described herein. After analysis of the Virtual Progeny, the results may be provided to the potential parents. The results may inform the potential parents of the chances that their future offspring will express one or more phenotypes, such as phenotypes described herein. In certain instances, the potential parents may also receive, for example, direct phone consultation with a genetic counselor employed by the company, or contact information for genetic counselors and/or other medical professionals who may provide the potential parents with follow up testing and consultation.

Virtual Progeny Assessment and Dating/Marriage Services

In other instances, the methods described herein may be used to allow for the evaluation of potential partners in connection with a matchmaking service. In one example, a Virtual Progeny assessment may be offered to a customer in connection with a matchmaking service, for example, through a single company or a co-marketing or partnership relationship. A user of a matchmaking service may order an assessment of Virtual Progeny described herein to determine the probability that an offspring resulting from the potential match between the user and a candidate partner will express one or more phenotypes described herein. The user may then use this information to aid in evaluating the candidate partner for a potential match. The matchmaking service may be an on-line service, such as Shaadi.com, eHarmony.com and Match.com.

In a particular application, assessment of Virtual Progeny begins with a customer order, where the customer pays a fee in exchange for the assessment. For example, a customer may be a user of a matchmaking service who is interested in evaluating another user for a suitable match. Such a customer may use an assessment of Virtual Progeny described herein to learn whether the potential offspring of a match between such customer and a candidate partner will express one or more phenotypes or traits, such as risk of disease. After selecting a candidate partner to evaluate, a customer may pay for both the customer's and the candidate partner's initial genomic scans with the candidate partner's consent. In other instances, the customer and the candidate partner may also pay separately for the initial genomic scans. After a customer places an order, DNA collection kits may be sent to the customer and the candidate partner, and the customer and the candidate partner may each deposit a biological sample into the collection kit. The collection kits may then be returned to the company for sending to a specialty lab or may be returned directly to the specialty lab for processing according to the methods described herein. A specialty lab, either internal within the company, contracted to work with the company, or external from the company, may perform genomic scans on the customer's and candidate partner's DNA from the provided sample and perform an assessment of Virtual Progeny using the methods described herein. The results of the assessment may then be provided to the customer and/or the candidate partner, and the customer and/or the candidate partner may use the results of the assessment in determining whether the other party is a suitable match.

Virtual Progeny Assessment and Sperm Donors/Egg Donors

In other applications, a female client seeking to have a child may have a Virtual Progeny assessment performed with one or more sperm donors to aid in selecting a donor. In one exemplary method, potential sperm donors are first recruited by a sperm bank. Donors who complete the screening process and are considered qualified by the sperm bank then provide a biological sample (such as a buccal swab) that may be processed to obtain whole DNA sequence, SNP genotypes, CNV genotypes or any other digital genetic information.

A female client also provides a biological sample, such as a buccal swab, which is used to generate a genome profile for the female client. The female client genome is then recombined computationally with each donor genome to generate a series of independent Virtual Progeny genomes, as described herein, representing each potential donor-client combination. Each Virtual Progeny genome may then be assessed for the probability of exhibiting one or more phenotypes, such as increased risk of disease. In certain instances, incompatible donor-client combinations are subtracted from the total donor pool to obtain a client-specific filtered donor pool, which may be used, e.g., as a starting point for further selection by the client. In other instances, a client may be given information on the probability of the incidence of one or more phenotypes from donor-client combinations, such as phenotypes preselected by the client, for further sperm donor selection by the client.

In other applications, a male client seeking to have a child may have a Virtual Progeny assessment performed with one or more egg donors to aid in selecting a donor. Egg donors may provide a biological sample (such as a buccal swab) to generate a genome profile for the egg donor, as described herein. The male client also provides a biological sample, such as a buccal swab, which is used to generate a genome profile for the male client. The male client genome is then recombined computationally with each egg donor genome to generate a series of independent Virtual Progeny genomes, as described herein, representing each potential donor-client combination. Each Virtual Progeny genome may then be assessed for the probability of exhibiting one or more phenotypes or traits, such as increased risk of disease. In certain instances, incompatible donor-client combinations are subtracted from the total donor pool to obtain a client-specific filtered donor pool, which may be used, e.g., as a starting point for further selection by the client. In other instances, a client may be given information on the probability of the incidence of one or more phenotypes from donor-client combinations, such as phenotypes preselected by the client, for further egg donor selection by the client.

In yet other applications, a heterosexual couple seeking to use a sperm or egg donor to have a child may use Virtual Progeny assessments to screen potential donors. For example, the couple may seek a sperm donor, and the female partner will be the genetic parent of offspring with the sperm donor. Alternatively, the couple may seek an egg donor, and the male partner will be the genetic parent of offspring with the egg donor. In such instances, two rounds of Virtual Progeny assessments may be performed. A first round of Virtual Progeny assessment is performed using biological samples from the heterosexual couple. A second round of Virtual Progeny assessment is performed between the genetic parent and one or more potential donors. The results of the first round of Virtual Progeny assessment may then be compared with the results of the second round, and a donor may be chosen whose Virtual Progeny exhibits an acceptable amount of matching in one or more phenotypes with the Virtual Progeny from the heterosexual couple.

In still other applications, a female homosexual couple seeking to use a sperm donor to have a child may use Virtual Progeny assessments to screen potential sperm donors. Only one of the female partners will be the genetic parent of offspring with the sperm donor. A first round of Virtual Progeny assessment is performed using biological samples from the homosexual couple. A second round of Virtual Progeny assessment is performed between the genetic female parent and one or more potential sperm donors. The results of the first round of Virtual Progeny assessment may then be compared with the results of the second round, and a sperm donor may be chosen whose Virtual Progeny exhibits an acceptable amount of matching in one or more phenotypes with the Virtual Progeny from the homosexual couple. In some situations, a Virtual Progeny assessment is also performed with the second female partner and one or more potential sperm donors, and a donor is selected whose Virtual Progeny exhibits an acceptable amount of matching in one or more phenotypes with the Virtual Progeny from the homosexual couple.

In yet other applications, a male homosexual couple seeking to use an egg donor to have a child may use Virtual Progeny assessments to screen potential egg donors. Only one of the male partners will be the genetic parent of offspring with the egg donor. A first round of Virtual Progeny assessment is performed using biological samples from the homosexual couple. A second round of Virtual Progeny assessment is performed between the genetic male parent and one or more potential egg donors. The results of the first round of Virtual Progeny assessment may then be compared with the results of the second round, and an egg donor may be chosen whose Virtual Progeny exhibits an acceptable amount of matching in one or more phenotypes with the Virtual Progeny from the homosexual couple. In some situations, a Virtual Progeny assessment is also performed with the second male partner and one or more potential egg donors, and a donor is selected whose Virtual Progeny exhibits an acceptable amount of matching in one or more phenotypes with the Virtual Progeny from the homosexual couple.

In further applications of the methods disclosed herein, the risk of disease in a potential progeny may be assessed, as well as the likelihood of expressing a genetically influenced trait or phenotype. As with the other methods disclosed, a first genomic DNA sample is obtained from a first potential parent and a second genomic DNA sample from a second potential parent. The presence or absence of one or more nucleotide variants are identified at one or more loci of at least one pair of chromosomes of the first and the second genomic DNA samples and these identified nucleotide variants for the first and second genomic DNA samples are compared to a plurality of predetermined genomic sequences of haplotypes having predetermined frequencies at predetermined loci to identify haplotypes present in the first and second genomic DNA samples. A first diploid genome profile for the first potential parent is constructed. The first genome profile comprises the identified haplotypes in the first genomic DNA sample and a linkage probability determined by the frequencies of the identified haplotypes in the plurality of predetermined genomic sequences. A second diploid genome profile for the second potential parent is constructed. The second genome profile comprises the identified haplotypes in the second genomic DNA sample and a linkage probability determined by the frequencies of the identified haplotypes in the plurality of predetermined genomic sequences. A first library is constructed that comprises potential haploid gamete genomes from the first diploid genome profile by generating a combination of the haplotypes identified in the first genomic DNA sample using the linkage probability for each combination of the identified haplotypes, while a second library is constructed that comprises potential haploid gamete genomes from the second diploid genome profile by generating a combination of the haplotypes identified in the second genomic DNA sample using the linkage probability for each combination of the identified haplotypes. The method also entails combining a first haploid gamete genome from the first library with a second haploid gamete genome from the second library to form a diploid progeny genome. The diploid progeny genome is compared to a database of genomes relating to disease-associated or genetically influenced phenotypes, thereby assessing the risk of disease or the likelihood of expressing a genetically influenced phenotypes of the potential progeny.

Computer Systems/Processors (the following computer systems/processors may be used in combination with, or as an alternative to, computer systems/processors described in reference to FIG. 5).

The methods and systems described herein may be used in combination with one or more processors, having either single or multiple cores. The processor may be operatively connected to a memory. For instance, the memory may be solid state, flash, or nanoparticle based. The processor and/or memory may be operatively connected to a network via a network adapter. The network may be digital, analog, or a combination of the two. The processor may be operatively connected to the memory to execute computer program instructions to perform one or more steps described herein. Any computer language known to those skilled in the art may be used.

Input/output circuitry may be included to provide the capability to input data to, or output data from, the processor and/or memory. For example, input/output circuitry may include input devices, such as keyboards, mice, touch pads, trackballs, scanners, and the like, output devices, such as video adapters, monitors, printers, and the like, and input/output devices, such as, modems and the like.

The memory may store program instructions that are executed by, and data that are used and processed by, CPUs to perform various functions. The memory may include electronic memory devices, such as random-access memory (RAM), read-only memory (ROM), programmable read-only memory (PROM), electrically erasable programmable read-only memory (EEPROM), and flash memory, and electro-mechanical memory, such as magnetic disk drives, tape drives, and optical disk drives, which may be used as an integrated drive electronics (IDE) interface, or a variation or enhancement thereof, such as enhanced IDE (EIDE) or ultra direct memory access (UDMA), or a small computer system interface (SCSI) based interface, or a variation or enhancement thereof, such as fast-SCSI, wide-SCSI, fast and wide-SCSI, etc, or a fiber channel-arbitrated loop (FC-AL) interface.

The systems described herein may also include an operating system that runs on the processor, including UNIX®, OS/2®, and WINDOWS®, each of which may be configured to run many tasks at the same time, e.g., a multitasking operating systems. In one aspect, the methods are utilized with a wireless communication and/or computation device, such as a mobile phone, personal digital assistant, personal computer, and the like. Moreover, the computing system may be operable to wirelessly transmit data to wireless or wired communication devices using a data network, such as the Internet, or a local area network (LAN), wide-area network (WAN), cellular network, or other wireless networks known to those skilled in the art.

In one embodiment, a graphical user interface may be included to allow human interaction with the computing system. The graphical user interface may comprise a screen, such as an organic light emitting diode screen, liquid crystal display screen, thin film transistor display, and the like. The graphical user interface may generate a wide range of colors, or a black and white screen may be used.

In certain instances, the graphical user interface may be touch sensitive, and it may use any technology known to skilled artisans including, but not limited to, resistive, surface acoustic wave, capacitive, infrared, strain gauge, optical imaging, dispersive signal technology, acoustic pulse recognition, frustrated total internal reflection, and diffused laser imaging.

The methods and compositions disclosed herein are further illustrated by the following examples. The examples are provided for illustrative purposes only. They are not to be construed as limiting the scope or content of the invention in any way.

Examples

Generation of Virtual Progeny Genome

In this particular example, the generation of a Virtual Progeny genome is a four step process. One of ordinary skill in the art will understand that other steps may be added, combined, or deleted as desired.

Step 1—Genome Scans

Processing is accomplished with the use of DNA microarrays, DNA sequencing protocols, or other DNA reading technologies. In the present example, a DNA microarray is used to generate information relating to loci of interest. This information is utilized to produce genome scans that include genotype information from the plurality of loci of interest, which are defined by single base polymorphisms ("SNPs or CNPs"), DNA sequence reads, copy number, or other forms of personal genetic information. In the present example, Jane Doe and John Smith provided samples, which have such information provided for loci 01 through N.

Step 2—Expansion of Genome Scans to Generate Genome Profiles

Existing population datasets, genome scans of family members, and a variety of computational tools and algorithms, known to those skilled in the art, may be used in combination with each person's genome scan to distinguish haplotypes, impute genotypes at additional loci, and establish long-range genetic phasing. The derived genome profile preferably incorporates phasing information in the form of stochastic matrices between haplotypes.

With genome scans performed on two or more related persons, phasing information is extended. In an example of genome analysis, the UCSC genome browser is used to display phasing over large maternally-inherited chromosomal segments that comprise 100 million base pairs or more. A Monte Carlo simulation or Markov process as described above is used to generate haplopaths through a genome, where haplotypes are transmitted intact, and stochastic matrices are used to move from one haplotype or locus to the next one. In the example, John Smith's genome is converted into a series of haplopaths by means of a Monte Carlo simulation.

Each individual genome profile is used to generate a pool of VirtualGametes.

Step 4—Virtual Progeny Permutations from Random Virtual Gametes from Each Individual Single Virtual Gametes from each person is chosen randomly and combined to produce one permutation of a Virtual Progeny genome. The process of Virtual Gamete choice and reproductive combination to produce a diploid genome is iterated a sufficient number of times such that the normalized sum of Virtual Progeny permutations provides a stable estimate of the Virtual Progeny genome probability distribution. For instance, the number of iterations may be between about 10 and about 100. More preferably, the number of iterations may be between about 100 and about 1000. Most preferably, the number of iterations may be between about 1000 and about 100,000. In another aspect, the number of iterations may be about 50 or greater. More preferably, the number of iterations may be about 150 or greater. Most preferably, the number of iterations may be about 3000 or greater.

In the above description, an embodiment is an example or implementation of the inventions. The various appearances of "one embodiment," "an embodiment" or "some embodiments" do not necessarily all refer to the same embodiments.

Although various features of the invention may be described in the context of a single embodiment, the features may also be provided separately or in any suitable combination. Conversely, although the invention may be described herein in the context of separate embodiments for clarity, the invention may also be implemented in a single embodiment.

Reference in the specification to "some embodiments", "an embodiment", "one embodiment" or "other embodiments" means that a particular feature, structure, or characteristic described in connection with the embodiments is included in at least some embodiments, but not necessarily all embodiments, of the inventions.

It is to be understood that the phraseology and terminology employed herein is not to be construed as limiting and are for descriptive purpose only.

The principles and uses of the teachings of the present invention may be better understood with reference to the accompanying description, figures and examples.

It is to be understood that the details set forth herein do not construe a limitation to an application of the invention.

Furthermore, it is to be understood that the invention can be carried out or practiced in various ways and that the invention can be implemented in embodiments other than the ones outlined in the description above.

It is to be understood that the terms "including", "comprising", "consisting" and grammatical variants thereof do not preclude the addition of one or more components, features, steps, or integers or groups thereof and that the terms are to be construed as specifying components, features, steps or integers.

If the specification or claims refer to "an additional" element, that does not preclude there being more than one of the additional element.

It is to be understood that where the claims or specification refer to "a" or "an" element, such reference is not be construed that there is only one of that element.

It is to be understood that where the specification states that a component, feature, structure, or characteristic "may", "might", "can" or "could" be included, that particular component, feature, structure, or characteristic is not required to be included.

Where applicable, although state diagrams, flow diagrams or both may be used to describe embodiments, the invention is not limited to those diagrams or to the corresponding descriptions. For example, flow need not move through each illustrated box or state, or in exactly the same order as illustrated and described.

Methods of the present invention may be implemented by performing or completing manually, automatically, or a combination thereof, selected steps or tasks.

The term "method" may refer to manners, means, techniques and procedures for accomplishing a given task including, but not limited to, those manners, means, techniques and procedures either known to, or readily developed from known manners, means, techniques and procedures by practitioners of the art to which the invention belongs.

The descriptions, examples, methods and materials presented in the claims and the specification are not to be construed as limiting but rather as illustrative only.

Meanings of technical and scientific terms used herein are to be commonly understood as by one of ordinary skill in the art to which the invention belongs, unless otherwise defined.

The present invention may be implemented in the testing or practice with methods and materials equivalent or similar to those described herein.

While the invention has been described with respect to a limited number of embodiments, these should not be construed as limitations on the scope of the invention, but rather as exemplifications of some of the preferred embodiments. Other possible variations, modifications, and applications are also within the scope of the invention. Accordingly, the scope of the invention should not be limited by what has thus far been described, but by the appended claims and their legal equivalents.

What is claimed is:

1. A computer-implemented method for accounting for genetic recombination in determining likelihood of unconceived progenies of two potential parents having a phenotype, the computer-implemented method, comprising:

receiving, by a computer, a first potential parent's diploid DNA profile and a second potential parent's diploid DNA profile, the first potential parent's diploid DNA profile and the second potential parent's diploid DNA profile generated respectively by DNA sequencing of a first biological sample of the first potential parent and a second biological sample of the second potential parent;

generating, by the computer, a plurality of virtual progenies of the first potential parent and the second potential parent, generating the plurality of virtual progenies accounted for genetic recombination and comprising:
for each virtual progeny:
generating a first virtual haplopath from the first potential parent's diploid DNA profile;
generating a second virtual haplopath from the second potential parent's diploid DNA profile, wherein each of the first virtual haplopath and the second virtual haplopath representing a virtual gamete simulated with genetic recombination, the virtual gamete comprising a plurality of genetic loci, each genetic locus having a haplotype and generated by progressing locus-by-locus of the first potential parent's diploid DNA profile and the second potential parent's diploid DNA profile to select, at least partially randomly and also based on linkage probability generated from linkage disequilibrium information, one of two alleles of the first potential parent's diploid DNA profile and the second potential parent's diploid DNA profile at each genetic locus; and
combining the first virtual haplopath and the second virtual haplopath to generate the virtual progeny;
determining, for each virtual progeny of the plurality of the virtual progenies that account for genetic recombination, a probability of the virtual progeny having the phenotype associated with a gene, the determining comprising:
a. assigning a score $s_i^P$ to each allele $h_i^P$ at the plurality of genetic loci (i) in each of the first virtual haplopath and the second virtual haplopath;
b. identifying a plurality of the alleles associated with the gene $Q_j$, the plurality of $N_j$ of the alleles $h_i^P$(k=1, ... , $N_j$) identified from the plurality of genetic loci (i) in the first and second virtual haplopaths;
c. mapping the scores $s_i^P$ to gene-specific scores $\bar{s}_{j,k}^P$ associated with gene $Q_j$ for the plurality of ($N_j$) alleles $h_k^P$; and
d. computing the probability of the virtual progeny having the phenotype associated with the gene to be a function of the gene-specific scores $\bar{s}_{j,k}^P$;
combining the determined probability of each virtual progeny of the plurality of the virtual progenies to generate a distribution; and
outputting a result of the likelihood of unconceived progenies of two potential parents having the phenotype based on the distribution, the result accounted for genetic recombination.

2. The method of claim 1, wherein the probability of having the phenotype is determined based on $P_j^P = 1 - \Pi_{k=1}^{Nj}[1 - \bar{s}_{j,k}^P]$.

3. The method of claim 1, wherein a probability of having a recessive phenotype is determined based on $p_j^{P1,P2} = (1 - \Pi_{k=1}^{Nj}[1 - \bar{s}_{j,k}^{P1}])(1 - \Pi_{k=1}^{Nj}[1 - \bar{s}_{j,k}^{P2}])$.

4. The method of claim 1, wherein a probability of having a dominant phenotype is determined based on $p_j^{P1,P2} = (1 - \Pi_{k=1}^{Nj}[1 - s_{j,k}^{P1}])(1 - \Pi_{k=1}^{Nj}[1 - \bar{s}_{j,k}^{P2}])$.

5. The method of claim 1, wherein each of the scores $s_i^P$ defines a likelihood that the allele $h_i^P$ is an amino acid substitution at the locus (i) that will damage protein function.

6. The method of claim 1, wherein each of the scores $s_i^P$ defines a probability that for a change in one or more amino acids that the change will occur randomly based on natural selection.

7. The method of claim 1, wherein the probability indicates a degree of expressivity of the phenotype in the virtual progeny.

8. The method of claim 1 further comprising comparing the probability to one or more thresholds to determine a category of expressivity of the phenotype.

9. The method of claim 1, wherein the probability corresponds to a probability of protein damage in one or more gene products, each associated with a single gene $Q_j$.

10. A computer-implemented method for accounting for genetic recombination in determining likelihood of unconceived progenies of two potential parents having a phenotype, the computer-implemented method, comprising:
receiving, by a computer, a first potential parent's diploid DNA profile and a second potential parent's diploid DNA profile, the first potential parent's diploid DNA profile and the second potential parent's diploid DNA profile generated respectively by DNA sequencing of a first biological sample of the first potential parent and a second biological sample of the second potential parent;
generating, by the computer, a plurality of virtual progenies of the first potential parent and the second potential parent, generating the plurality of virtual progenies accounted for genetic recombination and comprising:
for each virtual progeny:
generating a first virtual haplopath from the first potential parent's diploid DNA profile;
generating a first virtual haplopath from the first potential parent's diploid DNA profile;
generating a second virtual haplopath from the second potential parent's diploid DNA profile, wherein each of the first virtual haplopath and the second virtual haplopath representing a virtual gamete simulated with genetic recombination, the virtual gamete comprising a plurality of genetic loci, each genetic locus having a haplotype and generated by progressing locus-by-locus of the first potential parent's diploid DNA profile and the second potential parent's diploid DNA profile to select, at least partially randomly and also based on linkage probability generated from linkage disequilibrium information, one of two alleles of the first potential parent's diploid DNA profile and the second potential parent's diploid DNA profile at each genetic locus; and
combining the first virtual haplopath and the second virtual haplopath to generate the virtual progeny;
determining, for each virtual progeny of the plurality of the virtual progenies that account for genetic recombination, a probability of the virtual progeny having the phenotype associated with a gene, the determining comprising:
a. comparing genotypes of the virtual progeny to one or more databases of genotype-phenotype associations to determine a phenotype associated with database genotypes matching genotypes of the virtual progeny genome sampling G, wherein the phenotype is associated with a penetrance value;
b. generating, by a random number generator of the computer, a random number that is weighted by a bias factor that is biased to express or non-express with a non-equal probability according to a predefined bias ratio;

c. adjusting the penetrance value with a degree of expression of the phenotype in the virtual progeny based on the random number; and d. determining the probability of the virtual progeny having the phenotype based on the penetrance value;

combining the determined probability of each virtual progeny of the plurality of the virtual progenies to generate a distribution; and outputting a result of the likelihood of unconceived progenies of two potential parents having the phenotype based on the distribution, the result accounted for genetic recombination.

11. The method of claim 1, wherein progressing locus-by-locus of the first potential parent's diploid DNA profile and the second potential parent's diploid DNA profile to select, at least partially randomly and also based on the linkage probability generated from the linkage disequilibrium information, one of two alleles of the first potential parent's diploid DNA profile and the second potential parent's diploid DNA profile at each genetic locus comprises using an iteration of a Monte Carlo simulation or a chain generated through a Markov process.

12. The method of claim 1, wherein the first potential parent's diploid DNA profile is the first potential parent's genome profile and the second potential parent's diploid DNA profile is the second potential parent's genome profile.

13. The method of claim 10, wherein progressing locus-by-locus of the first potential parent's diploid DNA profile and the second potential parent's diploid DNA profile to select, at least partially randomly and also based on the linkage probability generated from the linkage disequilibrium information, one of two alleles of the first potential parent's diploid DNA profile and the second potential parent's diploid DNA profile at each genetic locus comprises using an iteration of a Monte Carlo simulation or a chain generated through a Markov process.

14. The method of claim 10, wherein the first potential parent's diploid DNA profile is the first potential parent's genome profile and the second potential parent's diploid DNA profile is the second potential parent's genome profile.

15. The method of claim 10, wherein a probability of having a recessive phenotype is determined based on $p_j^{p1,p2} = (1-\Pi_{k=1}^{Nj}[1-\bar{s}_{j,k}^{p1}])(1-\Pi_{k=1}^{Nj}[1-\bar{s}_{j,k}^{p2}])$.

16. The method of claim 10, wherein a probability of having a dominant phenotype is determined based on $p_j^{p1,p2} = (1-\Pi_{k=1}^{Nj}[1-\bar{s}_{j,k}^{p1}])(1-\Pi_{k=1}^{Nj}[1-\bar{s}_{j,k}^{p2}])$.

17. The method of claim 10, wherein the probability indicates a degree of expressivity of the phenotype in the progeny.

18. The method of claim 10 further comprising comparing the probability to one or more thresholds to determine a category of expressivity of the phenotype.

19. The method of claim 10, wherein the probability corresponds to a probability of protein damage in one or more gene products, each associated with a single gene.

20. The method of claim 1, wherein the phenotype is one of the following: Thalassemia, cystic fibrosis, anemia, or Mucopolysaccharidosis.

21. The method of claim 1, wherein each of the first virtual haplopath and the second virtual haplopath includes at least 10,000 base pairs.

22. The method of claim 1, wherein determining, for each virtual progeny of the plurality of the virtual progenies, the probability of the virtual progeny having the phenotype associated with a gene, further comprising:

generating, by a random number generator of the computer, a random number that is weighted by a bias factor that is biased to express or non-express with a non-equal probability according to a predefined bias ratio; and adjusting the probability of the virtual progeny having the phenotype associated with the gene based on the random number.

23. The method of claim 10, wherein the phenotype is one of the following: Thalassemia, cystic fibrosis, anemia, or Mucopolysaccharidosis.

24. The method of claim 10, wherein each of the first virtual haplopath and the second virtual haplopath includes at least 10,000 base pairs.

* * * * *